United States Patent
Zeitels et al.

(10) Patent No.: US 9,198,568 B2
(45) Date of Patent: Dec. 1, 2015

(54) METHODS AND SYSTEMS OF MATCHING VOICE DEFICITS WITH A TUNABLE MUCOSAL IMPLANT TO RESTORE AND ENHANCE INDIVIDUALIZED HUMAN SOUND AND VOICE PRODUCTION

(75) Inventors: Steven M. Zeitels, Newton, MA (US); Robert E. Hillman, Weston, MA (US); Sandeep Sidram Karajanagi, Malden, MA (US); Robert S. Langer, Newton, MA (US)

(73) Assignees: The General Hospital Corporation, Boston, MA (US); Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 13/579,347
(22) PCT Filed: Mar. 4, 2011
(86) PCT No.: PCT/US2011/027230
§ 371 (c)(1), (2), (4) Date: Oct. 31, 2012
(87) PCT Pub. No.: WO2011/109730
PCT Pub. Date: Sep. 9, 2011

(65) Prior Publication Data
US 2013/0041467 A1 Feb. 14, 2013

Related U.S. Application Data

(60) Provisional application No. 61/339,538, filed on Mar. 4, 2010.

(51) Int. Cl.
A61F 2/00 (2006.01)
A61B 1/267 (2006.01)
(Continued)

(52) U.S. Cl.
CPC ............... *A61B 1/2673* (2013.01); *A61L 27/26* (2013.01); *A61L 27/50* (2013.01)

(58) Field of Classification Search
CPC .................................. A61F 2/00; A61L 15/00
USPC ......... 623/14.11, 9; 424/93.1–93.7, 445, 484; 568/679, 852; 530/353–354, 356, 403; 536/30, 51, 55.1, 123.1; 514/2, 12, 514/44 R, 55–57
See application file for complete search history.

(56) References Cited

U.S. PATENT DOCUMENTS 2,898,898 A   8/1959   Burch
3,867,329 A   2/1975   Halpern et al.
(Continued)

FOREIGN PATENT DOCUMENTS

EP   0 637 450   2/1995
EP   0 815 177   1/1998
(Continued)

OTHER PUBLICATIONS

Bader et al., "A study of diffusion in poly(ethyleneglycol)-gelatin based semi-interpenetrating networks for use in wound healing," Polym. Bull., 2009, 62:381-389.
(Continued)

*Primary Examiner* — Yashita Sharma
(74) *Attorney, Agent, or Firm* — Fish & Richardson P.C.

(57) ABSTRACT

The disclosure relates to methods and systems for making customized treatments to a subject's vocal tissues to provide a desired level of vocal function.

25 Claims, 8 Drawing Sheets

(51) Int. Cl.
*A61L 27/26* (2006.01)
*A61L 27/50* (2006.01)

(56) References Cited

U.S. PATENT DOCUMENTS

| | | |
|---|---|---|
| 4,439,584 A | 3/1984 | Gould et al. |
| 5,733,562 A | 3/1998 | Lee |
| 5,749,968 A | 5/1998 | Melanson et al. |
| 5,763,399 A | 6/1998 | Lee |
| 5,844,016 A | 12/1998 | Sawhney et al. |
| 5,893,830 A | 4/1999 | Zeitels |
| 5,900,245 A | 5/1999 | Sawhney et al. |
| 5,919,702 A | 7/1999 | Purchio et al. |
| 6,051,248 A | 4/2000 | Sawhney et al. |
| 6,121,341 A | 9/2000 | Sawhney et al. |
| 6,214,331 B1 | 4/2001 | Vanderhoff et al. |
| 6,217,894 B1 | 4/2001 | Sawhney et al. |
| 6,352,710 B2 | 3/2002 | Sawhney et al. |
| 6,372,494 B1 | 4/2002 | Naughton et al. |
| 6,387,977 B1 | 5/2002 | Sawhney et al. |
| 6,432,437 B1 | 8/2002 | Hubbard |
| 6,455,600 B1 | 9/2002 | Hahnle et al. |
| 6,531,147 B2 | 3/2003 | Sawhney et al. |
| 6,537,574 B1 | 3/2003 | Hubbard |
| 6,544,503 B1 | 4/2003 | Vanderhoff et al. |
| 6,790,840 B1 | 9/2004 | Lee et al. |
| 6,949,625 B2 | 9/2005 | Tayot |
| 7,060,287 B1 | 6/2006 | Hubbard et al. |
| 7,073,294 B2 | 7/2006 | Yamaska et al. |
| 7,118,746 B1 | 10/2006 | Naughton et al. |
| 7,131,997 B2 | 11/2006 | Bourne et al. |
| 7,238,364 B2 | 7/2007 | Sawhney et al. |
| 7,311,861 B2 | 12/2007 | Lanphere et al. |
| 7,387,032 B2 | 6/2008 | Cliffon et al. |
| 7,412,978 B1 | 8/2008 | Keller |
| 2001/0000728 A1 | 5/2001 | Sawhney et al. |
| 2002/0064512 A1 | 5/2002 | Petersen et al. |
| 2002/0127266 A1 | 9/2002 | Sawhney et al. |
| 2003/0003436 A1 | 1/2003 | Willson et al. |
| 2003/0104032 A1 | 6/2003 | Sawhney et al. |
| 2003/0147835 A1 | 8/2003 | Munro et al. |
| 2003/0175410 A1 | 9/2003 | Campbell et al. |
| 2003/0233150 A1 | 12/2003 | Bourne et al. |
| 2004/0028676 A1 | 2/2004 | Klein et al. |
| 2004/0185021 A1 | 9/2004 | Hubbard |
| 2004/0191900 A1 | 9/2004 | Mizuno et al. |
| 2004/0234574 A9 | 11/2004 | Sawhney et al. |
| 2004/0242770 A1 | 12/2004 | Feldstein et al. |
| 2005/0074877 A1 | 4/2005 | Mao et al. |
| 2005/0142152 A1 | 6/2005 | Leshchiner et al. |
| 2005/0226935 A1 | 10/2005 | Kamath et al. |
| 2005/0238870 A1 | 10/2005 | Buiser et al. |
| 2005/0263916 A1 | 12/2005 | Lanphere et al. |
| 2005/0281866 A1 | 12/2005 | Jarrett et al. |
| 2005/0287180 A1 | 12/2005 | Chen et al. |
| 2006/0084759 A1 | 4/2006 | Calabro et al. |
| 2006/0094944 A1 | 5/2006 | Chuang et al. |
| 2006/0094945 A1 | 5/2006 | Barman et al. |
| 2006/0094946 A1 | 5/2006 | Kellogg et al. |
| 2006/0207343 A1 | 9/2006 | Clifton et al. |
| 2006/0233854 A1 | 10/2006 | Seliktar et al. |
| 2006/0233855 A1 | 10/2006 | Seliktar et al. |
| 2006/0246033 A1 | 11/2006 | Ninan et al. |
| 2007/0015908 A1 | 1/2007 | Fischer et al. |
| 2007/0020225 A1 | 1/2007 | Abramson et al. |
| 2007/0036745 A1 | 2/2007 | Leshchiner et al. |
| 2007/0059375 A1 | 3/2007 | Bourne et al. |
| 2007/0060998 A1 | 3/2007 | Butterwick et al. |
| 2007/0077232 A1 | 4/2007 | Naughton et al. |
| 2007/0141339 A1 | 6/2007 | Song et al. |
| 2007/0141340 A1 | 6/2007 | Song et al. |
| 2007/0142560 A1 | 6/2007 | Song et al. |
| 2007/0179605 A1 | 8/2007 | Myung |
| 2007/0212385 A1 | 9/2007 | David et al. |
| 2007/0225631 A1 | 9/2007 | Bowlin et al. |
| 2007/0270501 A1 | 11/2007 | Fitzgerald et al. |
| 2007/0280986 A1 | 12/2007 | Gil et al. |
| 2007/0283962 A1 | 12/2007 | Doshi et al. |
| 2008/0008647 A1 | 1/2008 | Richard et al. |
| 2008/0009902 A1 | 1/2008 | Hunter et al. |
| 2008/0009942 A1 | 1/2008 | Mizuno et al. |
| 2008/0032920 A1 | 2/2008 | Prestwich et al. |
| 2008/0038306 A1 | 2/2008 | David et al. |
| 2008/0041715 A1 | 2/2008 | Lanphere et al. |
| 2008/0045654 A1 | 2/2008 | Richard et al. |
| 2008/0152698 A1 | 6/2008 | Effing et al. |
| 2009/0042294 A1 | 2/2009 | Calabro et al. |
| 2009/0142309 A1 | 6/2009 | Calabro et al. |
| 2009/0143766 A1 | 6/2009 | Calabro et al. |
| 2009/0252700 A1 | 10/2009 | Zahos et al. |
| 2010/0055184 A1 | 3/2010 | Zeitels |

FOREIGN PATENT DOCUMENTS

| | | |
|---|---|---|
| EP | 0 927 214 | 7/1999 |
| EP | 1 178 812 | 2/2002 |
| EP | 1 534 351 | 6/2005 |
| EP | 1 870 115 | 12/2007 |
| JP | 2006-522851 | 10/2006 |
| WO | 96/29370 | 9/1996 |
| WO | 97/22372 | 6/1997 |
| WO | 98/08550 | 3/1998 |
| WO | 98/12243 | 3/1998 |
| WO | 98/17791 | 4/1998 |
| WO | 99/31167 | 6/1999 |
| WO | 00/44808 | 8/2000 |
| WO | 00/69449 | 11/2000 |
| WO | 01/96422 | 12/2001 |
| WO | 02/063270 | 8/2002 |
| WO | 03/079985 | 10/2003 |
| WO | 03/082359 | 10/2003 |
| WO | 2004/032713 | 4/2004 |
| WO | 2005/018612 | 3/2005 |
| WO | 2005/025493 | 3/2005 |
| WO | 2005/061018 | 7/2005 |
| WO | 2005/097677 | 10/2005 |
| WO | 2005/105906 | 11/2005 |
| WO | 2005/115489 | 12/2005 |
| WO | 2005/118128 | 12/2005 |
| WO | 2006/002050 | 1/2006 |
| WO | 2006/004951 | 1/2006 |
| WO | 2006/022671 | 3/2006 |
| WO | 2006/050031 | 5/2006 |
| WO | 2006/050032 | 5/2006 |
| WO | 2006/050033 | 5/2006 |
| WO | 2006/062253 | 6/2006 |
| WO | 2007/032565 | 3/2007 |
| WO | 2007/004437 | 4/2007 |
| WO | 2007/073553 | 6/2007 |
| WO | 2007/073554 | 6/2007 |
| WO | 2007/089864 | 8/2007 |
| WO | 2007/106457 | 9/2007 |
| WO | 2007/124132 | 11/2007 |
| WO | 2007/126411 | 11/2007 |
| WO | 2008/008859 | 1/2008 |
| WO | 2008/024640 | 2/2008 |
| WO | 2008/041846 | 4/2008 |

OTHER PUBLICATIONS

Cho et al., "A novel synthetic route for the preparation of hydrolytically degradable synthetic hydrogels," J Biomed Mater Res., 2009, 90A:1073-1082.

Munoz-Pinto et al., "Probing Vocal Fold Fibroblast Response to Hyaluronan in #D Contexts," Biotechnol. Bioeng., Nov. 1, 2009, 104(4):821-831.

European Office Action in Application No. 09 81 836.7, dated Apr. 18, 2013, 6 pages.

U.S. Office Action in U.S. Appl. No. 12/553,800, dated Mar. 30, 2012, 33 pages.

U.S. Office Action in U.S. Appl. No. 12/553,800, dated Jan. 7, 2013, 21 pages.

(56) References Cited

OTHER PUBLICATIONS

Abelson, M.B., et al., Clinical cure of bacterial conjunctivitis with azithromycin 1%: Vehicle-controlled, double-masked clinical trial. American Journal of Ophthalmology, 2008. 145(6): p. 959-965.
Adams, M.E. et al., "A risk-benefit of injections of Hyaluronan and its derivatives in the treatment of osteoarthritis of the knee," Drug Safety, 2000; 23:115-130.
Argentiere, S., et al., Synthesis of Poly(acrylic acid) Nanogels and Application in Loading and Release of an Oligothiophene Fluorophore and Its Bovine Serum Albumin Conjugate. Macromolecular Symposia, 2009. 281: p. 69-76.
Barbu, E., et al., Polymeric materials for ophthalmic drug delivery: trends and perspectives. Journal of Materials Chemistry, 2006. 16(34): p. 3439-3443.
Barr et al., Quality of life in children with velopharyngeal insufficiency. Arch Otolaryngol Head Neck Surg. Mar. 2007;133(3):224-9.
Bishop, Experimental Researches into the Physiology of the Human Voice. The London and Edinburgh Philosophical Magazine and Journal of Science. 1836.
Brunings et al., Eine neue Behandlungsmethode der Rekurrenslahmungen. Verhandl Deutsch Vereins Deutscher Laryngologen. 1911;18:93-151.
Brunings, W., Direct Laryngoscopy: Autoscopy by Counter-Pressure, in Direct Laryngoscopy, Bronchoscopy, and Epophagoscopy; 1912, Bailliere, Tindall & Cox; London; p. 110-115.
Burdick, J.A., et al, Stimulation of neurite outgrowth by neurotrophins delivered from degradable hydrogels. Biomaterials, 2006. 27(3): p. 452-459.
Burugapalli, K., V. Koul, and A.K. Dinda, Effect of composition of interpenetrating polymer network hydrogels based on poly(acrylic acid) and gelatin on tissue response: A quantitative in vivo study. Journal of Biomedical Materials Research Part A, 2004. 68A(2): p. 210-218.
Carpenter, C.P. and C.B. Shaffer, A study of the polyethylene glycols as vehicle for intramuscular and subcutaneous injection. Journal of the American Pharmaceutical Association—Scientific Edition, 1952. 41(1): p. 27-29.
Carpenter, C.P., et al, Response of dogs to repeated intravenous injection of polyethylene-glycol-4000 with notes on excretion and sensitization. Toxicology and Applied Pharmacology, 1971. 18(1): p. 35-40.
Caton et al., Viscoelasticity of hyaluronan and nonhyaluronan based vocal fold injectables: implications for mucosal versus muscle use. Laryngoscope. Mar. 2007;117(3):516-21.
Chan et al., Viscoelastic Shear Properties of Human Vocal Fold Mucosa: Measurement Methodology and Empirical Results; *J. Acoust. Soc. Am*. 106(4), Pt. 1, Oct. 1999; pp. 2008-2021.
Christensen, L., "Normal and pathologic tissue reactions to soft-tissue gel fillers," Dermatologic Surgery, 2007; 33:S168-S175.
Cobell et al., Fine needle aspiration of the vocal fold lamina propria in an animal model. Ann Otol Rhinol Laryngol. Oct. 2006;115(10):764-8.
Cobell et al., Fine needle aspiration: a novel application in laryngology. J Voice. Sep. 2007;21(5):617-22.
Connor et al., Attitudes of children with dysphonia. J Voice. Mar. 2008;22(2):197-209.
Cruise, G.M., et al., In vitro and in vivo performance of porcine islets encapsulated in interfacially photopolymerized poly(ethylene glycol) diacrylate membranes. Cell Transplantation, 1999.8(3): p. 293-306.
Delong et al., Covalently immobilized gradients of bFGF on hydrogel scaffolds for directed cell migration. Biomaterials. Jun. 2005;26(16):3227-34.
Duflo et al., Differential gene expression profiling of vocal fold polyps and Reinke's edema by complementary DNA microarray. Ann Otol Rhinol Laryngol. Sep. 2006;115(9):703-14.
Duflo et al., Effect of a synthetic extracellular matrix on vocal fold lamina propria gene expression in early wound healing. Tissue Eng. Nov. 2006;12(11):3201-7.
Duflo et al., Vocal fold tissue repair in vivo using a synthetic extracellular matrix. Tissue Eng. Aug. 2006;12(8):2171-80.
Elbert, D.l. and J.A. Hubbell, Conjugate addition reactions combined with free-radical cross-linking for the design of materials for tissue engineering. Biomacromolecules, 2001. 2(2): p. 430-41.
Ferguson et al., Time and dose effects of mitomycin C on extracellular matrix fibroblasts and proteins. Laryngoscope. Jan. 2005;115(1):110-5.
Fisher et al., Photoinitiated polymerization of biomaterials. Annu Rev Mater Res. 2001;31:171-181.
Gable, R.S., Comparison of acute lethal toxicity of commonly abused psychoactive substances. Addiction, 2004. 99(6): p. 686-696.
Gobin et al., Val-ala-pro-gly, an elastin-derived non-integrin ligand: smooth muscle cell adhesion and specificity. J Biomed Mater Res A. Oct. 1, 2003;67(1):255-9.
Goodyer et al., In Vivo Measurement of the Shear Modulus of the Human Vocal Fold: Interim Results From Eight Patients; *Eur Arch Otorhinolaryngol*, 2006; DOI 10.1007/s00405-006-0239-z.
Goodyer et al., The Shear Modulus of the Human Vocal Fold, Preliminary Results from 20 Larynxes, *Eur Arch Otorhinolaryngol*, 2007, 264:45-50.
Hahn, Collagen Composite Hydrogels for Vocal Fold Lamina Propria Restoration, Biomaterials 2006, 27(7):1104-9.
Hahn, M.S., et al., Glycosaminoglycan composition of the vocal-fold lamina propria in relation to function. Annals of Otology Rhinology and Laryngology, 2008. 117(5): p. 371-381.
Hansen et al., Current understanding and review of the literature: vocal fold scarring. J Voice. Mar. 2006;20(1):110-20.
Hansen et al., In vivo engineering of the vocal fold extracellular matrix with injectable hyaluronic acid hydrogels: early effects on tissue repair and biomechanics in a rabbit model. Ann Otol Rhinol Laryngol. Sep. 2005;114(9):662-70.
Herten, M., et al., Biodegradation of different synthetic hydrogels made of polyethylene glycol hydrogel/RGD-peptide modifications: an immunohistochemical study in rats. Clin. Oral Implants Res, 2009. 20(2): p. 116-25.
Hertgard et al., Cross-Linked Hyaluronan Versus collagen for Injection Treatment of Glottal Insufficiency: 2-Year Follow-up; *Acta Otolaryngol* 2004; 124:1208-1214.
Hetegard et al.; Cross-Linked Hyaluronan Used as Augmentation Substance for Treatment of Glottal Insufficiency: Safety Aspects and Vocal Fold Function; *Laryngoscope*. 2002, 112(12):2211-9.
Hillman, R.E., The Contempory Voice Laboratory: Its Role in the Diagnosis of Laryngeal Disorders, in Otolaryngology—Head and Neck Surgery Recertification Study Guide, J. Gluckman, Editor. 1999.
Hillman, R.E., W.M. Montgomery, and S.M. Zeitels, Current Diagnostics and Office Practice: Use of objective measures of vocal function in the multidisciplinary management of voice disorders. Current Opinion in Otolaryngology & Head and Neck Surgery 1997. 5(3): p. 172-175.
Hirano et al., Phonosurgery: Basic and Clinical Investigations. Otologia (Fukuoka). 1975;21:239-442.
Hirano et al., Structure of the vocal fold in normal and diseased states: anatomical and physical studies. Proceedings of the Conference on the Assessment of Vocal Pathology. The American Speech-Language-Hearing Association. 1981;11:11-27.
Hirano, S., et al, Growth factor therapy for vocal-fold scarring in a canine model. Annals of Otology Rhinology and Laryngology, 2004. 113(10): p. 777-785.
Hogikyan, N.D. and G. Sethuraman, Validation of an instrument to measure voice-related quality of life (V-RQOL). Journal of Voice, 1999. 13: p. 557-569.
Ifkovits, J.L and J.A. Burdick, Review: Photopolymerizable and degradable biomaterials for tissue engineering applications. Tissue Engineering, 2007.13(10): p. 2369-2385.
International Preliminary Report on Patentability; PCT/US2009/004974; Simin Baharlou; Mar. 8, 2011.
International Search Report and Written Opinion; PCT/US2009/004974; N.Y. Jang; Apr. 2010.
Jackson, C., Position of the Patient for Peroral Endoscopy, in Peroral Endoscopy and Laryngeal Surgery. 1915, Laryngoscope Co.: St. Louis. p. 77-88.

(56) References Cited

OTHER PUBLICATIONS

Jia et al., Hyaluronic Acid-Based Microgels and Microgel Networks for Vocal Fold Regeneration; *Biomacromolecules* 2006, 7, pp. 3336-3344.
Jia et al., Synthesis and Characterization of in Situ Cross-Linkable Hyaluronic Acid-Based Hydrogels with Potential Application for Vocal Fold Regeneration; *Macromolecules* 2004, 37, pp. 3239-3248.
Jones, A.W. and P. Holmgren, Comparison of blood-ethanol concentration in deaths attributed to acute alcohol poisoning and chronic alcoholism. Journal of Forensic Sciences, 2003. 48(4): p. 874-879.
Jones, D.S., et al., Physicochemical characterization of bioactive polyacrylic acid organogels as potential antimicrobial implants for the buccal cavity. Biomacromolecules, 2008.9(2): p. 624-633.
Kass, E.5., Hillman, R.E., Zeitels, S.M., The Submucosal Infusion Technique in Phonomicrosurgery. Annals of Otology, Rhinology, & Laryngology, 1996. 105: p. 341-347.
Kempster, G., et al., Consensus Auditory-Perceptual Evaluation of Voice: Development of a Standardized Clinical Protocol American Journal of Speech-Language Pathology, 2009. 18(2): p. 124-132.
Kim et al., Synthesis and evaluation of novel biodegradable hydrogels based on poly(ethylene glycol) and sebacic acid as tissue engineering scaffolds. Biomacromolecules. Jan. 2008;9(1):149-57.
Kizilel et al., Sequential formation of covalently bonded hydrogel multilayers through surface initiated photopolymerization. Biomaterials. Mar. 2006;27(8):1209-15.
Kizilel, S., V.H. Perez-Luna, and F. Teymour, Photopolymerization of poly(ethylene glycol) diacrylate on eosin-functionalized surfaces. Langmuir, 2004. 20(20): p. 8652-8658.
Klemuk, Viscoelastic Properties of Three Vocal-Fold Injectable Biomaterials at Low Audio Frequencies; Laryngoscope Sep. 2004; 114(9):1597-603.
Ko et al., Photo-Crosslinked Porous PEG Hydrogel Membrane Via Electrospinning. J. Photopolym Sci Technol. 2006;19(3):413-18.
Kriesel et al., Treatment of vocal fold scarring: rheological and histological measures of homologous collagen matrix. Ann Otol Rhinol Laryngol. Oct. 2002;111(10):884-9.
Kutty, J.K. et al.; Mechanomimetic Hydrogels for Vocal Fold Lamina Propria Regeneration; J. Biomat.; Sci Polym. Ed. 2009, 20(5-6) p. 737-56.
Kutty, J.K.; Vibration stimulates vocal mucosa-like matrix expression by hydrogel-encapsulated ; J tissue Eng Regen Med.; 2010;4(1) 62-72.
Kutty, K.J., et al., The effect of hyaluronic acid incorporation on fibroblast spreading and proliferation within PEG-diacrylate based semi-interpenetrating networks. Biomaterials, 2007. 28(33): p. 4928-4938.
Leach et al., Characterization of Protein Release from Photocrosslinkable Hyaluronic Acid-Polyethylene Glycol Hydrogel Tissue Engineering Scaffolds; *Biomaterials*, 2005, 26, 125-135.
Liao, Influence of Hydrogel Mechanical Properties and Mesh Size on vocal Fold Fibroblast Extracellular Matrix Production and Phenotype, Acta Biometer. 2008; 4(5) 1161-71.
Mehta, D.D., et al, Voice production mechanisms following phonosurgical treatment of early glottic cancer. Annals of Otology, Rhinology & Laryngology, 2010. 119: p. 1-9.
Moon et al., Promotion of endothelial tubulogenesis with Ephrin A1 and EphB4 conjugated to synthetic hydrogels. FASEB J. Mar. 6, 2006;20(4):A12.
Myung, D. et al.; Biomimetic strain hardening in interpenetrating polymer network hydrogels; ScienceDirect; vol. 48, Issue 18; Aug. 24, 2007, p. 5376-5387.
Nuttelman et al., The effect of ethylene glycol methacrylate phosphate in PEG hydrogels on mineralization and viability of encapsulated hMSCs. Biomaterials. Mar. 2006;27(8):1377-86.
Orlandi et al., Microarray analysis of allergic fungal sinusitis and eosinophilic mucin rhinosinusitis. Otolaryngol Head Neck Surg. May 2007;136(5):707-13.
Park, V.D., N. Tirelli, and J.A. Hubbell, Photopolymerized hyaluronic acid-based hydrogels and interpenetrating networks. Biomaterials, 2003. 24(6): p. 893-900.
Prestwich et al., Injectable synthetic extracellular matrices for tissue engineering and repair. Adv Exp Med Biol. 2006;585:125-33.
Ramanan et al., Development of a temperature-sensitive composite hydrogel for drug delivery applications. Biotechnol Prog. Jan.-Feb. 2006;22(1):118-25.
Rousseau et al., Experimentally induced phonation increases matrix metalloproteinase-1 gene expression in normal rabbit vocal fold. Otolaryngol Head Neck Surg. Jan. 2008;138(1):62-8.
Rousseau, B., et al, Characterization of vocal-fold scarring in a canine model. Laryngoscope, 2003. 113(4): p. 620-627.
Roy S., et al., Polymers in Mucoadhesive Drug-Delivery Systems: A Brief Note. Designed Monomers and Polymers, 2009. 12(6): p. 483-495.
Roy, N., et al., Voice disorders in the general population: prevalence, risk factors, and occupational impact. Laryngoscope, 2005.115(11): p. 1988-95.
Scalco, A.N., Shipman, W.F., Tabb, H.G., Microscopic Suspension Laryngoscopy. Annals of Otology, Rhinology, & Laryngology, 1960. 69: p. 1134-1138.
Scherzer, T. and U. Decker, Kinetic investigations on the UV-induced photopolymerization of a diacrylate by time-resolved FTIR spectroscopy: the influence of photoinitiator concentration, light intensity and temperature. Radiation Physics and Chemistry, 1999. 55(5-6): p. 615-619.
Shaffer, C.B. and F.H. Critchfield, The Absorption and Excretion of the Solid Polyethylene Glycols (Carbowax Compounds). Journal of the American Pharmaceutical Association—Scientific Edition, 1947. 36(5): p. 152-157.
Shaffer, C.B., F.H. Critchfield, and C.P. Carpenter, Renal Excretion and Volume Distribution of Some Polyethylene Glycols in the Dog. American Journal of Physiology, 1948. 152(1): p. 93-99.
Si, E.C., et al., Ocular Pharmacokinetics of AzaSite Xtra-2% Azithromycin Formulated in a DuraSite Delivery System. Current Eye Research, 2009. 34(6): p. 485-491.
Smyth, H.F., C.P. Carpenter, and C.B. Shaffer, The Toxicity of High Molecular Weight Polyethylene Glycols—Chronic Oral and Parenteral Administration. Journal of the American Pharmaceutical Association—Scientific Edition, 1947. 36(5): p. 157-160.
Taite et al., Bioactive hydrogel substrates: probing leukocyte receptor-ligand interactions in parallel plate flow chamber studies. Ann Biomed Eng. Nov. 2006;34(11):1705-11.
Thibeault et al., Comparison of telomere length of vocal folds with different tissues: a physiological measurement of vocal senescence. J Voice. Jun. 2006;20(2):165-70.
Thibeault et al., Gene expression changes of inflammatory mediators in posterior laryngitis due to laryngopharyngeal reflux and evolution with PPI treatment: a preliminary study. Laryngoscope. Nov. 2007;117(11):2050-6.
Thibeault et al., Inflammatory cytokine responses to synthetic extracellular matrix injection to the vocal fold lamina propria. Ann Otol Rhinol Laryngol. Mar. 2008;117(3):221-6.
Thibeault et al., Informed consent in otolaryngology research. Otolaryngol Head Neck Surg. Nov. 2005;133(5):651-3.
Thibeault, Advances in our understanding of the Reinke space. Curr Opin Otolaryngol Head Neck Surg. Jun. 2005;13(3):148-51.
West, J.L. et al., "Separation of the arterial wall from blood contact using hydrogel barriers reduces intimal thickening after balloon injury in the rat: the roles of medial and luminal factors in arterial healing," Proc. Natl. Acad. Sci., USA, 1996; 93:13188-93.
Williams, C.G., et al., Variable cytocompatibility of six cell lines with photoinitiators used for polymerizing hydrogels and cell encapsulation. Biomaterials, 2005. 26(11): p. 1211-1218.
Wlotzka et al., In vivo properties of an anti-GnRH Spiegelmer: an example of an oligonucleotide-based therapeutic substance class. Proc Natl Acad Sci U S A. Jun. 25, 2002;99(13):8898-902.
Working, P.K., et l., Safety of poly(ethylene glycol) and poly(ethylene glycol) derivatives, in Poly(Ethylene Glycol), Chemistry and Biological Applications, J.M. Harris and S. Zalipskv, Editors. 1997. p. 45-57.
Ylitalo et al., Relationship between time of exposure of laryngopharyngeal reflux and gene expression in laryngeal fibroblasts. Ann Otol Rhinol Laryngol. Oct. 2006;115(10):775-83.

(56) References Cited

OTHER PUBLICATIONS

Zeitels et al., Foresight in laryngology and laryngeal surgery: a 2020 vision. Ann Otol Rhinol Laryngol. 2007;116(Supplement 198):1-16.
Zeitels et al., Laryngology and phonosurgery. N Engl J Med. Aug. 28, 2003;349(9):882-92.
Zeitels et al., Phonomicrosurgery in singers and performing artists: treatment outcomes, management theories, and future directions. Ann Otol Rhinol Laryngol. 2002;111(Supplement 190):21-40.
Zeitels et al., Phonosurgical reconstruction of early glottic cancer. Laryngoscope. Oct. 2001;111(10):1862-5.
Zeitels et al., sulcus, scar, synechia, and web. In Atlas of Phonomicrosurgery and Other Endolaryngeal Procedures for Benign and Malignant Disease. 2001; Singular, San Diego:133-151.
Zeitels et al., Voice and treatment outcome from phonosurgical management of early glottic cancer. Ann Otol Rhinol Laryngol. 2002;111(Supplement 190):1-20.
Zeitels, S.M., A Universal Modular Glottiscope System: The Evolution of a Century of Design and Technique for Direct Laryngoscopy. Annals of Otology, Rhinology and Laryngology, 1999. 108{Supplement 179): p. 1-24.
Zeitels, S.M., Burns, J. A., Dailey, S. H., Suspension laryngoscopy revisited. Annals of Otology, Rhinology, & Laryngology, 2004. 113(1): p. 16-22.
Zeitels, S.M., Premalignant epithelium and microinvasive cancer of the vocal-fold: The evolution of phonomicrosurgical management. Laryngoscope, 1995. 105 {Supplement 67): p. 1-51.
Zeitels, S.M., Vaughan, C.W., "External Counter-Pressure" and "Internal Distension" for Optimal Laryngoscopic Exposure of the Anterior Glottal Commissure. Annals of Otology, Rhinology & Laryngology, 1994. 103: p. 669-675.
Zeitels, S.M., Vaughan, C.W., A submucosal vocal-fold infusion needle. Otolaryngology: Head and Neck Surgery, 1991. 105: p. 478-479.
Hertegard et al., Otolaryngol Head Neck Surg., 128(3):401-406 (2003).
International Preliminary Report on Patentability; PCT/US2011/027230; Sep. 4, 2012.
Supplementary European Search Report; EP 09 81 1836; Feb. 21, 2013; D. Werner; pp. 1-3.
Chan et al., "Hyaluronic Acid (With Fibronectin) As a Bioimplant for the Vocal Fold Mucosa," Laryngoscope, 109:1142-1149 (Jul. 1999).
Klemuk et al., "Viscoelastic Properties of Three Vocal-Fold Injectable Biomaterials at Low Audio Frequencies," Laryngoscope, 114:1597-1603 (Sep. 2004).
Supplementary European Search Report issued in EP09811836 on Feb. 21, 2013.
U.S. Office Action in U.S. Appl. No. 12/553,800, dated Oct. 27, 2014, 20 pages.

METHODS AND SYSTEMS OF MATCHING VOICE DEFICITS WITH A TUNABLE MUCOSAL IMPLANT TO RESTORE AND ENHANCE INDIVIDUALIZED HUMAN SOUND AND VOICE PRODUCTION

CROSS REFERENCE TO RELATED APPLICATION

This application is a 371 application of International Application No. PCT/US2011/027230, filed on Mar. 4, 2011, and claims priority to U.S. Provisional Patent Application No. 61/339,538, filed on Mar. 4, 2010, the disclosure of which is incorporated herein by reference in its entirety.

FIELD OF THE INVENTION

This disclosure relates to methods and systems for using an implant to treat vocal dysfunction that are tailored, or adjusted, for the vocal needs and deficits of individual subjects.

BACKGROUND

Voice loss is universal throughout the world, irrespective of age, gender, or social stratification and has a negative impact on effectiveness at work, in addition to being detrimental to psychosocial health. The importance of a reliable human voice has become increasingly critical in our age of communication. A healthy voice will likely become even more crucial in the 21st century; presently, greater than 80 percent of jobs in the United States are communication-based. A vocal deficit can be extremely disabling, and this will be more evident as voice-recognition becomes a driver for many information and communication technologies, i.e., replacing manual inputting (typing). Haxer, M., Guinn, L., and Hogikyan, N., *Use of speech recognition software: A vocal endurance test for the new millennium*? Journal of Voice, 15: 231-236 (2001). Furthermore, because of the unique nature of vocal performance, singing and/or oration are revered in a majority of primitive and modern societies. This is illustrated by the veneration ascribed to the religious leader, educator, entertainer, and at times the politician. Zeitels, S. M., Healy, G. B., *Laryngology and Phonosurgery*. New England Journal of Medicine, 349(9):882-92 (2003).

Optimal voice (laryngeal) sound production requires apposition of the vocal fold (cord) edges (glottal valve), which are driven into entrained oscillation by the sustained subglottal aerodynamic pressure and air flow from the tracheo-bronchial tree (FIG. 1A). The actual sound (acoustic signal) of the voice is produced by the air pulses that are emitted as the vocal folds open and close the glottis (opening between the vocal folds) during vibration. Ideal entrained vibration requires smooth vocal edges which close evenly, and which retain supple pliability. The vocal fold edges are covered by mucous membrane (mucosa), which are comprised of an outer epithelium and a superficial lamina propria (SLP), which lies just under the epithelium as shown in FIG. 1B. The epithelium has negligible rheologic properties and assumes the vibratory characteristics of whatever material lies beneath. Normal vocal fold vibration is manifested primarily as a wave of displaced mucosal tissue (SLP and epithelium) on the surface of the vocal folds, i.e., the mucosal wave. Presence of an intact mucosal wave is a primary sign of normal vocal fold structure and function. Since the SLP accounts for a majority of vocal fold vibration, loss of pliability of this layer due to the formation of stiff fibrosis or scar causes deterioration in vibratory function and associated hoarse voice (dysphonia). Laryngeal stroboscopy and high-speed videoendoscopy allows for clinical assessment of phonatory-mucosal vocal-fold vibration/oscillation and thereby assess the biomechanical behavior of phonatory mucosal layered microstructure, epithelium, and superficial lamina propria.

Voice production is optimal when the phonatory mucosa of both vocal folds retains favorable biomechanical/rheologic properties including elasticity and viscosity. This allows for efficient translation of the power source (aerodynamic pressure and flow) into an acoustic signal (voice). In a normal phonatory system, the vocal folds (glottis) are the sound source, while the pharynx, oral cavity, and nose function as a complex supraglottal resonating chamber, which individualizes a human's vocal signature.

From the initial cries at birth, through one's final words, the typical collision forces and shearing stresses sustained by the phonatory mucosa of vocal folds through life probably comprise the most substantial long-term soft-tissue trauma in the human body. A majority of the cases of untreatable hoarseness are due to diminished pliability of phonatory mucosa. There are likely more than 5 million individuals in the United States with this problem at any given time. However, the largest majority will never seek care and consider their vocal dysfunction to be their vocal signature/variation, because it is so commonplace and there is no remedy for this vocal insufficiency. This mucosal deficit is even incorrectly considered to be a normal component of the aging voice. Ironically, this dysfunctional mucosal soft tissue is often the result of decades of voice use (long-term trauma) rather than intrinsic age-related senescent tissue deterioration. Essentially, humans accumulate vocal mileage resulting in phonatory mucosal soft-tissue trauma during their activities in life. Those who are effusive and/or have vocally-demanding lives are prone to wear out and injure the phonatory tissues more rapidly. Given 21st century voice requirements, phonatory mucosal stiffness is increasingly impairing and terminating the career of voice professionals such as teachers, managers, executives, politicians, and performing artists.

Impliable (stiff) phonatory mucosa is also often associated with a variety of lesions such as polyps, cancer, nodules, and cysts, and vocal-fold membranes with these disorders are referred to as being "scarred." Scarred phonatory mucosa can also result from prolonged endotracheal intubation, as well as from the treatment of carcinoma (surgery or radiation) or laryngotracheal stenosis. There is a large population of adolescent and young adults who have undergone airway reconstruction as infants or children. These elegant procedures that were designed in the 1970s, and modified in the 1980s, have allowed these children to function without an artificial airway. However, a majority of them have some type of vocal dysfunction. Smith, M. E., et al., *Voice problems after pediatric laryngotracheal reconstruction: videolaryngostroboscopic, acoustic, and perceptual assessment*. Int J Pediatr Otorhinolaryngol, 25(1-3):173-81 (1993). This dysfunction is typically the result of the unavoidable placement of life-preserving artificial airways and the subsequent reconstructive airway procedures.

SUMMARY OF THE INVENTION

This disclosure relates, inter alia, to the discovery that if one categorizes a desired or realistic level of vocal function for an individual (e.g., a subject) and selects a particular tunable implant, such as a hydrogel composition, with a specific elastic shear modulus (G') and residence time after implantation, then one can provide a customized treatment specific to the subject's vocal dysfunction and needs.

In one aspect, this disclosure features methods of providing a customized treatment to a subject, by selecting a vocal implant to produce an approximate desired level of vocal function in the subject.

In another aspect, this disclosure features methods that include (a) assessing the subject's vocal mechanism to determine the primary mode of sound production and identify deficits in vocal function; (b) determining a level of vocal function that can be attained for the subject after successful treatment; (c) selecting a specific implant with a certain in vivo residence time based on the determined level of vocal function, wherein the implant provides an in vivo residence time after implantation of at least one day; and (d) administering the implant to one or more subepithelial locations in the subject's larynx or pharynx phonatory mucosa to provide a customized treatment specific to the subject's anatomy and needs.

In yet another aspect, this disclosure features methods of making the implants recited herein. The methods include but are not limited to (a) forming an aqueous solution including an initiator, and a predetermined ratio of a crosslinkable polymer and a non-crosslinkable polymer; (b) crosslinking the crosslinkable polymer to form a hydrogel composition; and (c) shearing the hydrogel composition.

Embodiments can include one or more of the following features.

The vocal implant can be selected based on an assessment of the subject's vocal mechanism, the subject's vocal needs, or both. The assessing can determine a primary mode of sound production, a deficit in structural anatomy, or a deficit in vocal function. For example, the assessing can use any one or more of: high-speed endoscopic laryngeal imaging, laryngeal stroboscopy, acoustic and aerodynamic measures of vocal function, and self-reporting of the impact of the vocal deficit on daily function using a standardized self-assessment scale (e.g., a standardized questionnaire and/or interview).

The deficits in structural anatomy or vocal function can be due to at least one of an anatomical structure that is missing, that is functionally impaired, or both. For example, the deficits in structural anatomy or vocal function can be due to at least one of a loss of muscle, loss of ligament, and loss of the superficial lamina propria of normal phonatory mucosa. The deficits can be corrected by the vocal implant. For example, the method can further include implanting the selected implant in a location within the subject that achieves the desired level of vocal function. The vocal implant is tunable based on the assessing. When the deficits are corrected, the vocal implant can produce the approximate desired level of vocal function.

The method can include placing the vocal implant under (e.g., immediately under) the epithelium of a region of the subject's supraglottis or pharynx in a location and in an amount that provides aerodynamically-driven mucosal vibration, such that the supraglottal or pharyngeal mucosa is converted into a phonatory sound source. In some embodiments, the implant can be administered to a location that can be within the phonatory mucosa of a vocal cord; superficial to the vocal ligament and beneath, e.g., deep to, the phonatory epithelium layer of a vocal cord; beneath or within the supraglottic (false cord, aryepiglottic fold, or corniculate region) mucosal layer that is serving as the phonatory sound source in patients who have lost vocal cord function as their site of voice production; and/or beneath or within the pharyngeal mucosal layer, which is serving as the phonatory sound source in patients who have had their larynx removed (total laryngectomy).

The vocal implant can be a liquid, a gel, or a solution of a polymer. The vocal implant can have an elastic shear modulus (G') within a range of 0 to 150 pascals (e.g., 0 to 50 pascals, 50 to 100 pascals, 100 to 150 pascals, 50 to 150 pascals, or 0 to 100 pascals). The vocal implant can have an in vivo residence time that is inversely related to the elastic shear modulus (G') of the vocal implant.

In some embodiments, the subject can have a complete loss of laryngeal sound production due to a total laryngectomy. For such a person, in some embodiments, the vocal implant for vibrating pharyngeal mucosa can include a hydrogel composition having an in vivo residence time of approximately four to six months, or six months or more, or at least four months (e.g., at least six months, at least 8 months, or at least one year).

The subject can be a voice user whose primary source of income is not from vocal performance, but who must use his/her voice for daily communication to fulfill occupational and personal responsibilities. For such a person, the vocal implant can include a hydrogel composition that has an in vivo residence time of approximately two to four months (e.g., approximately two months, approximately three months, approximately four months, approximately two to three months, approximately three to four months, approximately two to four months or more, approximately two to six months or more).

The subject can be a singer or an actor whose primary source of income is from vocal performance. For such a person, the vocal implant can include a liquid or a hydrogel composition that has an in vivo residence time of approximately one day to two months. The determined level of vocal function for a singer or actor is success in vocal performance that is commensurate with the subject's role or song, type of engagement obligation along with their level of talent and experience.

In preferred embodiments, the implant can include a hydrogel composition. The hydrogel composition can have an elastic shear modulus of 0 to 150 Pascals. In some embodiments, the hydrogel can have an elastic shear modulus of 0 to 50 Pascals and an in vivo residence time of approximately one day to two months; an elastic shear modulus of 50 to 100 Pascals and an in vivo residence time of approximately two months to four months; or an elastic shear modulus of from 100 to 150 Pascals and an in vivo residence time of approximately four to six months or more.

The vocal implant can include a network of one or more polymers, such that the vocal implant can include at least a crosslinked polymer, or a crosslinked polymer and a non-crosslinked polymer. For example, when the vocal implant includes a hydrogel, the hydrogel can include a semi-interpenetrating polymer network of a crosslinked polymer and a non-crosslinkable polymer, such as a polyethylene glycol derivative and a non-crosslinkable polymer (e.g., a polyethylene glycol). The crosslinked polymer can include an acrylate derivative and the non-crosslinkable polymer can include a water-soluble polymer. For example, the crosslinked polymer can include at least one of hyaluronic acid methacrylate, crosslinkable derivatives of dextrans, crosslinkable derivatives of hyaluronic acid, crosslinkable derivatives of alginates, crosslinkable derivatives of gelatins, crosslinkable derivatives of elastins, crosslinkable derivatives of collagens, crosslinkable derivatives of celluloses, crosslinkable derivatives of methylcelluloses, crosslinkable derivative of polyalkylene glycol, crosslinkable derivative of polyethylene glycol, and polyethylene glycol diacrylate; and the non-crosslinked polymer is selected from the group consisting of any one or more of polyethylene glycol (PEG), poly(lysine), hyaluronic acid (HA), dextrans, alginates, gelatins, elastins, collagens, celluloses, methylcelluloses, derivatives thereof, and combinations thereof.

In some embodiments, the crosslinked polymer can include hyaluronic acid methacrylate, acrylated derivatives of dextrans, acrylated derivatives of hyaluronic acid, acrylated derivatives of alginates, acrylated derivatives of gelatins, acrylated derivatives of elastins, acrylated derivatives of collagens, acrylated derivatives of celluloses, acrylated derivatives of methylcelluloses, acrylated derivative of polyalkylene glycol, acrylated derivative of polyethylene glycol, polyethylene glycol diacrylate (PEG-DA), and combinations thereof; and the non-crosslinkable polymer is selected from the group consisting of any one or more of polyethylene glycol (PEG), poly(lysine), hyaluronic acid (HA), dextrans, alginates, gelatins, elastins, collagens, celluloses, methylcelluloses, derivatives thereof, and/or combinations thereof.

The non-crosslinkable polymer can include polysaccharides (e.g., hyaluronic acid, dextran, and/or alginate), water-soluble polymers (e.g., poly(ethylene glycol)), and proteins (e.g., poly-lysine, and/or collagen) their derivatives, and/or combinations thereof. For example, the non-crosslinkable polymer can include poly(ethylene glycol), hyaluronic acid, alginate, poly(lysine), and/or dextran. The water-soluble polymer (e.g., the non-crosslinkable polymer) can include polyethers, polyols, poly(amino acids), proteins, polypeptides, polyamides, and polysaccharides, such as polyethylene glycol (PEG), poly(lysine), hyaluronic acid (HA), dextrans, alginates, gelatins, elastins, collagens, cellulose, methylcellulose, and derivatives thereof.

In some embodiments, prior to crosslinking, the poly(ethylene glycol) derivative can include poly(ethylene glycol) diacrylate. The poly(ethylene glycol) derivative can have a number average molecular weight of from 100 Da to 50,000 Da. The non-crosslinkable poly(ethylene glycol) can have a number average molecular weight of from 100 Da to 50,000 Da.

The hydrogel can further include a biologically active agent. For example, the hydrogel can include or be joined with a biologically active agent that: enhances permanent or temporary phonatory mucosal pliability and vibratory function; enhances treatment of a disease or lesion; enhances healing after surgery or trauma; inhibits inflammation, edema, or swelling; inhibits fibrosis and/or scar formation; prolongs the residence time of the implant; and/or that enhances the pliability of the implant to improve vocal fold vibration.

In some embodiments, the biologically active agent includes or is joined with one or more living cells or cell types. The living cells or cell types can enhance permanent or temporary phonatory mucosal pliability and vibratory function; enhance treatment of a disease or lesion; enhance healing after surgery or trauma; inhibit inflammation, edema, or swelling; inhibit fibrosis and/or scar formation; prolong the residence time of the implant.

The biologically active agent can include pharmaceutical agents (e.g., a small molecule drug, or a dendrimer), an anti-fibrotic agent, an anti-proliferative agent, an anti-inflammatory agent, a cell (e.g., a stem cell, vocal fold fibroblast, skin fibroblast), a polynucleotide (e.g., a gene or DNA or RNA), a protein, and a peptide. The biologically active agent can be encapsulated in a nanoparticle or a microparticle before encapsulation in the gel.

In some embodiments, when making the vocal implant, the initiator is a photoinitiator and crosslinking includes irradiating the aqueous solution with UV light. Making the vocal implant can include passing the hydrogel composition through a needle. In some embodiments, shearing further includes successively passing the hydrogel through at least one additional needle having a smaller bore size than a preceding needle.

"Biocompatible" refers to a material that is substantially nontoxic to a recipient's cells in the quantities and at the location used, and also does not elicit or cause a significant deleterious or untoward effect on the recipient's body at the location used, e.g., an unacceptable immunological or inflammatory reaction, unacceptable scar tissue formation, etc.

"Biodegradable" means that a material is capable of being broken down physically and/or chemically within cells or within the body of a subject, e.g., by hydrolysis under physiological conditions and/or by natural biological processes such as the action of enzymes present within cells or within the body, and/or by the action of cells within the body such as phagocytosis and/or by processes such as dissolution, dispersion, etc., to form smaller chemical species which can typically be metabolized and, optionally, used by the body, and/or excreted or otherwise disposed of. For purposes of the present disclosure, a polymer or hydrogel whose mass decreases over time in vivo due to a reduction in the number of monomers and/or due to the actions of the cells in the body is considered biodegradable. In certain embodiments, the hydrogel useful in vocal cord repair is not substantially biodegradable.

A "biologically active agent" is any compound or agent, or its pharmaceutically acceptable salt, which possesses a desired biological activity, for example therapeutic, diagnostic, and/or prophylactic properties in vivo. It is to be understood that the agent may need to be released from the hydrogel in order for it to exert a biological activity. Biologically active agents include, but are not limited to, therapeutic agents as described herein. Biologically active agents may be, without limitation, small molecules, peptides or polypeptides, immunoglobulins, e.g., antibodies, nucleic acids, cells, tissue constructs, etc. Without limitation, hormones, growth factors, drugs, cytokines, chemokines, clotting factors and endogenous clotting inhibitors, etc., are biologically active agents.

The term "crosslinked" as used herein describes a polymer with at least one covalent bond that is not found in the repeating units of the polymer or found between repeating units of the polymer. The crosslinking bonds are typically between subject strands or molecules of the polymer; however, intramolecular crosslinking to form macrocyclic structures may also occur. The crosslinks are formed between any two functional groups of the polymer (e.g., at the ends, on the side chains, etc.). In certain embodiments, the crosslinks are formed between terminal acrylate units of the polymers. Also, any type of covalent bond may form the crosslink (e.g., carbon-carbon, carbon-oxygen, carbon-nitrogen, oxygen-nitrogen, sulfur-sulfur, oxygen-phosphorus, nitrogen-nitrogen, oxygen-oxygen, etc.). The resulting crosslinked material may be branched, linear, dendritic, etc. In certain embodiments, the crosslinks form a 3-D network of crosslinks. The crosslinks may be formed by any chemical reaction that results in the covalent bonds. Typically, the crosslinks are created by free radical initiated reactions, for example, with a photoinitiator or thermal initiator.

A "hydrogel" is a three-dimensional network including hydrophilic polymers that contains a large amount of water. A hydrogel may, for example contain 30%, 40%, 50%, 60%, 70%, 80%, 90%, 95%, or an even greater amount of water on a w/w basis. A "hydrogel precursor" is a polymer that is at least partly soluble in an aqueous medium and is capable of becoming crosslinked to form a hydrogel.

"Interpenetrating network" refers to any material with a network of polymers where two or more polymers are cross-linked in the presence of each other. The polymers are cross-linkable, and each forms its own network by cross-linking with itself but not with the other polymer(s). Typically, the two or more polymers are synthesized and/or cross-linked in the presence of each other, the polymers have similar kinetics, and the two polymers are not dramatically phase separated.

"Semi-interpenetrating network" refers to a network of polymers where one polymer is cross-linked with itself in the presence of a non-crosslinkable polymer(s).

"Solubility" refers to the amount of a substance that dissolves in a given volume of solvent at a specified temperature and pH to form a saturated solution. Solubility may be determined, for example, using the shake-flask solubility method (ASTM: E 1148-02, Standard Test Method for Measurements of Aqueous Solubility, Book of Standards Volume 11.05). For example, solubility may be determined at a pH of 7.0 and at a temperature of 37° C.

"Subject," as used herein, refers to an individual to whom a vocal implant is to be delivered. Subjects are humans, but can be other mammals, particularly domesticated mammals (e.g., dogs, cats, and birds), or primates. A subject under the care of a physician or other health care provider may be referred to as a "patient."

The "swelling ratio" is a measure of the amount of water absorbed into a hydrogel after incubation and indirectly reflects the proportion of a cross-linked polymer in the hydrogel. The swelling ratio is calculated as the ratio between hydrated gel weight and dehydrated gel weight using lyophilization for drying.

"Pharmaceutical agent," also referred to as a "drug," is used herein to refer to an agent that is administered to a subject to treat a disease, disorder, or other clinically recognized condition that is harmful to the subject, or for prophylactic purposes, and has a clinically significant effect on the body to treat or prevent the disease, disorder, or condition. Therapeutic agents include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th edition (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005.

"Viscosity" refers to a measurement of the thickness or resistance to flow of a liquid at a given temperature. Viscosity may be determined using a variety of methods and instruments known in the art. For example, a polymer is first weighed and then dissolved in an appropriate solvent. The solution and viscometer are placed in a constant temperature water bath. Thermal equilibrium is obtained within the solution. The liquid is then brought above the upper graduation mark on the viscometer. The time for the solution to flow from the upper to lower graduation marks is recorded. Viscosity of a solution including a polymer may be determined in accordance with ASTM Book of Standards, Practice for Dilute Solution Viscosity of Polymers (ASTM D2857), Volume 08.01, June 2005 or relevant ASTM standards for specific polymers. Solubility may be tested at a temperature of between 20 and 40° C., e.g., approximately 25-37° C., e.g., approximately 37° C., or any intervening value of the foregoing ranges. For example, solubility may be determined at approximately pH 7.0-7.4 and approximately 37° C.

"Elastic shear modulus" (G') of a material is a mathematical description of a material's tendency to be deformed elastically (i.e., non-permanently) when a force is applied parallel to one of its surfaces while its opposite face experiences an opposing force (e.g., friction). Elastic shear modulus is calculated as the ratio of shear stress to shear strain. For example, if a force of 1 N is applied tangentially (on the xy plane) to a surface of an area of 1 $m^2$ and produces a change in the shape by 1% (strain=0.01) in the xy plane, then the elastic shear modulus of the material is 1/0.01=100 Pa.

"Viscous shear modulus" (G") of a material is a mathematical description of a material's tendency to dissipate energy (in the form of heat) when a force is applied parallel to one of its surfaces while its opposite face experiences an opposing force (e.g., friction).

"In vivo residence time" (also referred to herein as "residence time") of an implant material is the length of time post-implantation at which the implant material has degraded and/or dissipated to the point that it can no longer be detected using standard techniques (e.g., histological analysis, microscopic analysis). The degradation or dissipation of the implant material can be estimated by implanting a predetermined amount of the implant material on a dorsal surface of an adult female New Zealand White Rabbit, recovering the implant after a period of time (e.g., 12 hours, one day, one week, a month, two months, or four months), and analyzing the tissue response to the implant using histological analysis, for example, as described in Example 6, infra. The duration until complete degradation or dissipation of the implant can be linearly extrapolated from the remaining implant material that is recovered from the rabbit model. Without wishing to be bound by theory, it is believed that in some instances, a degradation rate can increase as degradation proceeds, while in other instances, a degradation rate can decrease as degradation proceeds, but an average degradation rate can be estimated using a linear extrapolation model. In some embodiments, more than one sample of a predetermined amount of the implant material can be implanted at different locations on a dorsal surface of an adult female New Zealand White Rabbit, and samples can be removed, e.g., without euthanizing the rabbit, from one or more locations at different periods of time and analyzed (e.g., histologically, microscopically) for degradation and/or dissipation. A degradation curve can be obtained and extrapolated to obtain the length of time post-implantation at which the implant material has degraded and/or dissipated to the point that it can no longer be detected using standard techniques. In some embodiments, when an implanted material has degraded and/or dissipated in a subject's vocal area, the subject's vocal defects can correspond to their pre-implantation conditions as assessed by the methods described, infra.

"Phonation" refers to the physical act of producing a vocal sound by using an air stream to vibrate mucosal tissue at a constriction in the upper aerodigestive tract. The actual sound is produced by the pulsing of air that results as the constriction opens and closes. This is normally accomplished by vocal fold vibration in the larynx, but can also involve mucosal vibration at other sites in the aerodigestive tract such as the supraglottis, upper subglottis and pharynx.

"Phonatory mucosa" refers to mucous membrane of the larynx or pharynx of a subject that serves as an aerodynamically-driven sound source. If a subject has an anatomically intact vocal fold structure, the phonatory mucosa refers to the musculo-membranous region of the vocal fold responsible for glottal sound production. It is comprised of an epithelium in this region and an underlying superficial lamina propria. If the vocal fold structure has been impaired or lost (e.g., due to cancer or trauma), the compensatory laryngeal sound source is likely to be the supraglottic larynx such that, in this scenario, phonatory mucosa is likely comprised of epithelium and subepithelial soft tissue of the false cords, aryepiglottic folds, or corniculate region. If the larynx has been removed (e.g., by a total laryngectomy), the phonatory mucosa will comprise vibrating mucous membranes in the pharynx induced by swallowing air (esophageal speech) or by means of a tracheo-esophageal prosthesis.

"Mucosal wave" refers to the wave of displaced mucosal tissue on the surface of the vocal folds during normal voice production. The mucosal wave accounts for a majority of vocal fold vibratory motion and is a primary indicator of normal vocal fold structure and function. Vibratory mucosa is mostly comprised of a soft and pliable layer of superficial lamina propria (SLP) with a thin covering of epithelium that essentially encapsulates the SLP substrate and thereby reflects its biomechanical properties.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the disclosure will be apparent from the following detailed description, and from the claims.

BRIEF DESCRIPTION OF THE DRAWINGS

FIG. 4A shows the calf larynx with vocal cords and an injection needle being moved into the vicinity of the injection site; FIG. 4B shows the injection of a dyed hydrogel composition (dotted area) into the right vocal cord; and FIG. 4C shows the adduction of the vocal cords using a clamp to apply sufficient pressure to the right and left arytenoids to cause the right and left vocal cords to contact each other.

DETAILED DESCRIPTION

Figure 1A:
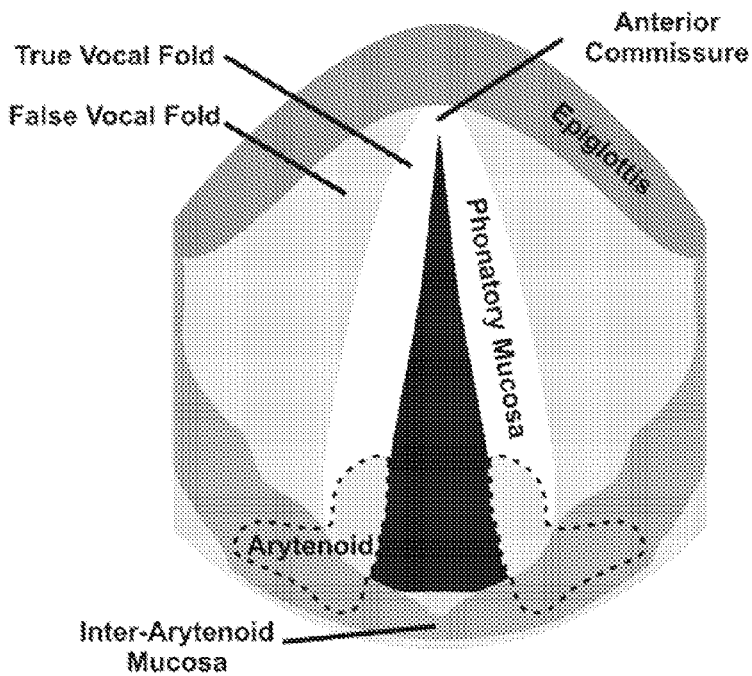
FIG. 1A is a schematic representation of a cephalad view of the laryngeal introitus and vocal folds from the oropharynx. The top of the figure is cephalad anatomically.
Figure 1B:
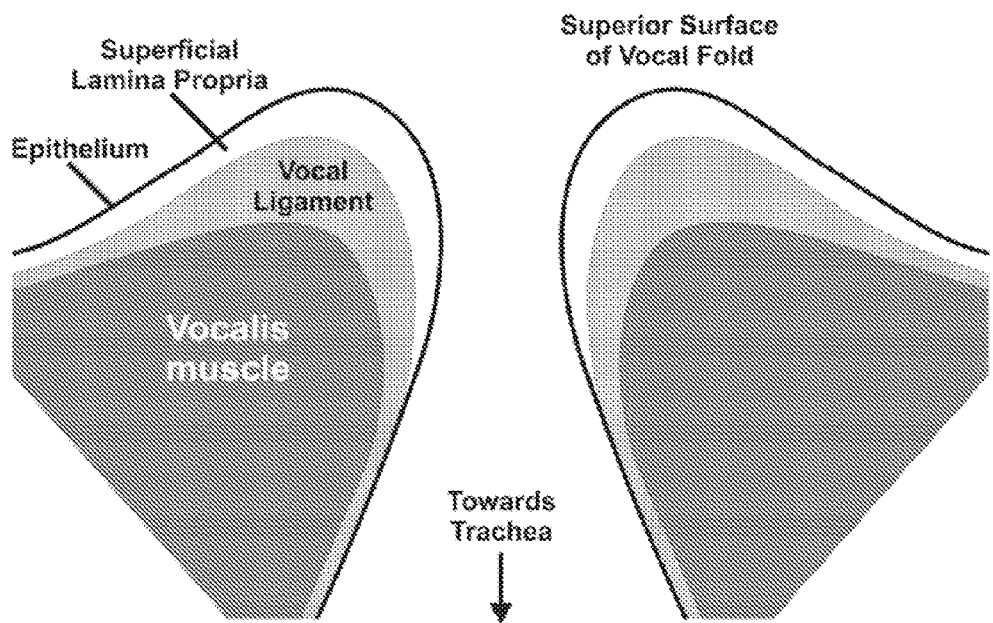
FIG. 1B is a schematic representation of a coronal section of the vocal folds showing their layered micro-structure during phonation at low pitch. The top of the figure is cephalad anatomically.
Figure 1C:
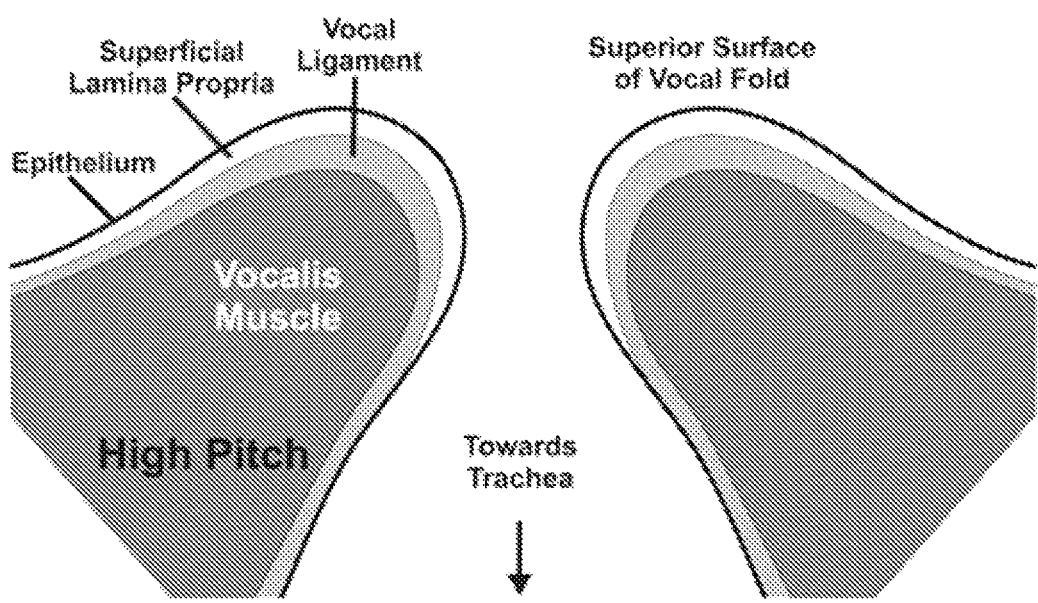
FIG. 1C is a schematic representation of a coronal section of the vocal folds showing their layered micro-structure during phonation at high pitch. Note the thinned superficial lamina propria layer. The top of the figure is cephalad anatomically.

This disclosure relates to systems and methods for assessing the level of vocal dysfunction for a specific individual patient and determining the desired level of vocal function in accordance with the residence-time capabilities of vocal implants, then determining the specific vocal implant, such as a tunable vocal hydrogel composition, required to achieve the desired level of vocal function, and then delivering that specifically tuned vocal implant into the proper location in the patient, e.g., within the subepithelial layer of the laryngeal or pharyngeal sound source. This is most frequently the musculo-membranous region of the vocal fold that is normally comprised of the superficial lamina propria (SLP).

Vocal implants, e.g., tunable vocal hydrogel compositions, as described herein have specific functional characteristics that allow them to be used to supplement the pliability of the phonatory mucosa of a subject with scarred or otherwise impaired vocal folds (VF) or other mucosa of the larynx or pharynx to support or enhance voice function. The constituent layer of the phonatory mucosa in vocal folds that has lost (or simply lacks sufficient) pliability is the superficial lamina propria (SLP). The new therapeutic and vocal enhancement methods described herein involve inserting or injecting a tailor-made vocal implant subepithelially into the region of the dysfunctional SLP within the phonatory mucosa that has diminished functional vibratory capacity, which may result from trauma {voice overuse, instrumentation, smoking}, disease or neoplasia, and/or treatment of these disorders. Placement (e.g., injection) of a subepithelial bioimplant supports phonatory mucosal pliability and enhanced vocal-fold vibration, thereby reducing stiffness and the associated hoarseness. As necessary, a less pliable biomaterial commensurate with the rheologic characteristics of vocal muscle and with a longer residence time can be placed in the deeper aspect of the residual vocal cord (paraglottic region). This is typically done to reconstruct the non-vibratory region of the vocal cord such as might be done for reconstruction after vocal-cord cancer treatment. (Zeitels S M, Jarboe, J., Franco, R. A. Phonosurgical Reconstruction of Early Glottic Cancer. *Laryngoscope* 2001; 111:1862-1865)

The vocal implants described herein possess unique physical and chemical characteristics and have been designed to act as an implant based on favorable viscoelastic properties. Specifically, the vocal implants must generally have a residence time of at least one day after implantation. The residence times can also be categorized as ranges of 1 day to 2 months, 2 months to 4 months, and 4 to 6 months or more, which are appropriate for different categories of patients. A residence time of less than 2 weeks (e.g., 1 or 2 days, or 1 to 2 weeks) may be useful, e.g., in people who have extreme and acute vocal needs despite deterioration that can be acute (e.g., upper respiratory tract infection) or chronic long-term phonatory mucosal stiffness. These scenarios occur with but are not limited to singers, actors, executives, sports announcers, politicians before key performances, meetings, speeches, and the like. In these cases, it may be acceptable for the residence time of the vocal implant to be less than 2 weeks.

The vocal implants may contain one or more active agents, such as pharmaceutical agents (e.g., anti-inflammatory or anti-angiogenic agents) that may be released immediately upon implantation or over an extended period of time. The vocal implant may even serve as a carrier and/or scaffold for living cells with the implant retaining biomechanical/rheological properties that quickly restore vocal-fold vibration, while the cells naturally regenerate the normal extracellular matrix proteins of the superficial lamina propria capable of permanent and long-term normal phonatory mucosal restoration.

The vocal implants are capable of simulating the rheological properties of the healthy phonatory mucosal SLP to thereby restore or enhance the pliability of phonatory mucosa, and can thus remedy most human hoarseness. Remarkably, these vocal implants can also enhance and improve human voice production subsequent to partial or total removal of the vocal cords or even the larynx. This includes patients producing voice from vibration of supraglottic mucosa subsequent to loss of vocal folds to cancer or trauma. Even patients who have undergone total laryngectomy can produce voice by airflow-induced vibration of pharynx mucosa from swallowing air (esophageal speech) (Solis-Cohen, J., *Pharyngeal Voice: Illustrated by Presentation of a Patient Who Phonates Without a Larynx and Without the Use of the Lungs*. Trans. Amer. Laryngological Assoc., 15: 114-116, 1983) or tracheo-esophageal puncture airflow diversion prostheses (Blom, E. D., Singer, M. I., *Tracheostoma vent and voice prosthesis*. Laryngoscope, 93(4):525-6, 1983). Increasing the pliability of supraglottic or pharyngeal mucosa would greatly enhance those cancer patients' voice production.

The actual length of time that the vocal implant has an impact on phonatory function is related primarily to the residence time of the implant material, but may also be influenced by any variations in the local biological response to the implant that different subjects might display. The basic specification of residence times for different formulations of vocal implants (e.g., hydrogels) is determined in an animal model. The functional impact of implants is determined by periodic comprehensive assessment of vocal function.

General Methodology

The vocal implants, e.g., vocal hydrogel compositions, have the capability of being tailored or tuned for a variety of patients' voice needs and requirements. This includes individualizing the mucosal rheology for different forms of voice production based on anatomico-physiological deficits regardless of whether the sound source is the vocal cords, supraglottal mucosal soft tissue (subsequent to partial laryngectomy), or alaryngeal pharyngeal mucosal vibration (subsequent to total laryngectomy). Understandably, voice-related mucosal mechanical requirements comprise a spectrum of viscoelastic properties varying from the voice needs of the greatest singers to cancer patients without a larynx, who vibrate pharyngeal mucosa.

In these widely disparate circumstances, the vocal implants that are most pliable might be expected to be mechanically optimal in all cases, however typically pliability (and elastic shear modulus) is inversely related to residence time and biomechanical performance must be integrated with a residence time that is matched to individual needs and circumstances. Therefore, the vocal implants described herein can be tailored to optimally titrate increased pliability with longer residence time. It is clear to those skilled in the art that there will be ongoing development of highly-pliable and well-tolerated implants that have increasing and longer residence times. Even these vocal implants, such as the vocal hydrogel compositions described herein, which have tunable properties that provide a selection of best pliability vs. longest residence-time, need to be individualized to serve the needs of different patients. For example, extremely pliable vocal implants designed to serve a singer, who requires multiple octaves of range, can have a residence time of one night or several weeks. This is in sharp contrast to a hydrogel composition designed to support a narrow frequency/pitch range associated with mucosal vibration from the supraglottis or pharynx (no vocalis muscle), which will have as substantially longer residence time.

Therefore, the present disclosure includes, inter alia, methods for using comprehensive information about patients' modes of voice production (e.g., vocal folds, supraglottic mucosa, pharyngeal mucosa) and associated vocal deficits (e.g., abnormal vocal function test results, negative impact on daily function), in combination with realistic estimates of vocal needs/goals, as a basis for selecting a composition of a specific vocal implant, e.g., vocal hydrogel composition, that provides a residence time for the requirements of a patient's needs.

The selected vocal implant, e.g., vocal hydrogel composition can be sheared during preparation because when it is then inserted, e.g., injected, into the vocal fold, it must flow easily and evenly through a thin needle. Furthermore, the shearing effect that occurs during injection of a patient should not negatively impact the functionality and residence time.

The implant should degrade slowly enough so that the residence time is sufficient, while minimizing permanent effects at the injection site so that it can be re-injected repeatedly. The vocal implants, e.g., vocal hydrogel compositions, described herein have the capability of integrating into residual native SLP while having minimal negative impact on residual vibratory function.

These principles of the advantages of a tunable vocal implant are illustrated by varying clinical scenarios. A post-laryngectomy patient may tolerate a stiffer material with a longer residence time (>4 months) since their vocal system does not have the capability of wide pitch variation. An educator who must demonstrate some emotion (e.g., enthusiasm, passion, and satisfaction), but not necessarily extremely wide pitch variation would be optimally treated with moderate pliability and moderate residence time (replacement at 2-4 months). A high performance vocalist would select the most pliable material that might require replacement every few days (e.g., one day, two days, three days, four days, five days) to weeks (e.g., one, two, three, four, or five weeks) during a period of recording or an intense tour or performance schedule.

The basic steps required to achieve a desired vocal treatment (e.g., therapeutic treatment or vocal enhancement) tailored to a specific subject include:

(1) comprehensive assessment of the subject's vocal mechanism to determine the primary mode of sound production (glottis, supraglottis, upper subglottis, pharynx) and identify deficits in vocal function;

(2) estimating a realistic level of vocal function that can be attained for the subject following successful treatment;

(3) selecting a specific vocal hydrogel composition; and (4) administering the proper volume of the vocal hydrogel composition to the precise sub-epithelial location(s) in the phonatory mucosa to provide a tailored treatment specific to the subject's vocal mechanism, level of vocal dysfunction, and vocal needs.

Methods and Systems for Assessing a Person's Vocal Mechanism, Vocal Deficit, and Vocal Needs A battery of assessment methods can be used to comprehensively describe a patient's vocal mechanism, vocal deficits, and realistic vocal needs/goals. These assessment methods are also used at follow up visits to assess the functional impact of the vocal hydrogel injection and help determine when re-injection is necessary.

(1) A standardized self-assessment can be done using a standard questionnaire and interview questions to gather information about a subject's medical history, vocal needs including, occupation, and descriptions of vocational and avocational voice use. For example, the questionnaire and interview can include questions about the subject's present difficulty, changes in circumstances that occurred with the onset of vocal difficulty, the subject's present voice condition, and the patient's vocal symptoms (e.g., hoarseness, breathiness in speaking voice, fatigue, voice breaks, loss of voice, trouble speaking softly, trouble singing, sore throat, tickling or choking sensation, lump in throat, difficulty swallowing, voice is lower, voice is higher, voice is weaker, vocal strain, frequent throat clearing, frequent dry throat, frequent coughing, nasality, difficulty with the telephone, and periods of normal voice).

The questionnaire and interview can also include questions about a subject's voice use, such as average voice use during a day, vocal activities (e.g., singing, acting, parent to young children, lecturing/teaching/speaking for an audience, cheerleader, clergy activities, caretaker for someone with a hearing impairment, phone operator, speaking over background noise, auctioneer, throat clearing, choral director, excessive coughing, sports enthusiast, imitating other people's voices, yelling/screaming, making "noises" with your voice, whispering, voice use with strenuous exercise (e.g., running), politician, or other).

Questions about a subject's past medical history can also be part of the questionnaire and interview. For example, the questions can relate to past surgery to the larynx, thyroid surgery, adenoidectomy, tonsillectomy, hysterectomy, radiation, oral surgery, tracheotomy, heart surgery, lung Surgery, appendectomy, kidney surgery, or other procedure(s). Questions about recent CT/MRI imaging, general medical conditions (e.g., high blood pressure/hypertension, heart disease, high cholesterol, thyroid disease, head/neck injury, cancer, pneumonia, bronchitis, sinus problems, medically diagnosed depression, gastroesophageal/laryngopharyngeal reflux, birth defect/syndrome such as cleft palate/lip palate, neurological impairment, communication disorder such as fluency/language/articulation/hearing/aphasia, environmental allergies, allergies to medications, tuberculosis, hepatitis, AIDS/HIV or other autoimmune disease, syphilis, asthma, or other), current medications, can be included. In addition, a subject's voice therapy history, alcohol consumption, smoking history, recreational drug use, caffeine consumption, and water consumption, pregnancy or menopause status, voice change during menstrual cycle, can form part of the questionnaire and interview.

The subject's voice-related quality of life measure can be assessed using a questionnaire that grades the subjects vocal problems on a scale, such as a 1-5 scale, where 1 corresponds to none (not a problem), 2 corresponds to a small amount, 3 corresponds to a moderate (medium) amount, 4 corresponds to a lot, and 5 corresponds to a problem that is as "bad as it can be." For example, the quality of life parameters can include: trouble speaking loudly or being heard in noisy situations, running out of air and needing to take frequent breaths when talking, not knowing what the voice would sound like when speaking, anxiety or frustration due to the subject's voice, depression because of the subject's voice, trouble using the telephone because of the subject's voice, trouble practicing the subject's profession because of the voice, avoiding social interactions due to the voice, repeating speech to be understood, and becoming less outgoing because of the subject's voice.

(2) Office-based transoral (rigid) and transnasal (flexible) endoscopy is used to assess the structure of the vocal mechanism. Endoscopy is typically coupled with videostroboscopy to obtain an estimate of vibratory function for vocal mechanisms that have sufficient periodicity for stroboscopic imaging. High-speed imaging (typically 2,000-6,000 images per second) is used to obtain detailed information about the true underlying vibratory function of the sound source, particularly for the type of aperiodic phonation that is often associated with voice disorders. Imaging of vibratory function is used to identify/pinpoint areas of phonatory mucosa that have diminished pliability and should be targeted for the injection of a vocal hydrogel. In cases of vocal sources that do not involve two vocal cords (e.g., vibration supraglottal, upper subglottal, or pharyngeal mucosa), accurate imaging of tissue vibration (stroboscopy or high-speed photography) is particularly critical for identifying the location and function of the primary sound source so that vocal hydrogels can be optimally positioned.

(3) Acoustic Measures: High quality digital audio recordings are obtained from subjects in a sound-treated room using a head-mounted condenser microphone while they perform a standard set of voice and speech tasks that are representative of their vocal demands (singing, lecturing, conversational speech, etc.). The microphone signal is calibrated for sound pressure level (dB) and then recorded/digitized and analyzed using commercial and customized computer software to yield measures of fundamental frequency (average, highest and lowest) and sound pressure level (average, highest and lowest). Hillman, R. E., W. M. Montgomery, and S. M. Zeitels, *Current Diagnostics and Office Practice: Use of objective measures of vocal function in the multidisciplinary management of voice disorders. Current Opinion in Otolaryngology & Head and Neck Surgery* 1997. 5(3): p. 172-175.

(4) Aerodynamic Measures: Digital recordings of non-invasive measures of intra-oral air pressure and the acoustic signal are obtained in a sound-treated room as subjects produce a specially-designed speech task (strings of "pa" syllables) as softly as possible without whispering. The recordings are analyzed using commercial and customized software to yield estimates of sound pressure level (db SPL) and lung phonation threshold air pressure (estimated from intra-oral air pressure during lip closure for the p-sound).

Methods for Selecting a Vocal Hydrogel to Treat a Subject

Information from the interview about the patient's vocal demands along with laryngoscopic, acoustic, and/or aerodynamic assessments, e.g., as described herein, are used to choose a vocal implant with a G' specification and associated residence time that is best suited to meet the needs of the patient as illustrated in Table 1.

TABLE 1

| Residence Time | Implant G' | Implant Location | Vocal Demands | Pitch Range (Octaves) | Maximum Loudness (dB)[1] | Phonation Threshold Pressure (kPa) |
|---|---|---|---|---|---|---|
| | 0 | | | | | |
| ≥1 day | ↑↓ | Vocal fold | Singing Performance | ≥2.0 | ≥90 | ≤0.5 |
| | 50 | | | | | |
| ≥2 months | ↑↓ | Vocal fold | Lecturing | ≥0.5 | ≥80 | ≤1.0 |
| | 100 | | | | | |
| ≥4 months | ↑↓ | Supraglottal, Upper subglottal or Pharyngeal | Conversation | ≤0.5 | ≥70 | ≥1.0 |
| | 150 | | | | | |

[1]Measured at 15 cm from the lips.

Referring to Table 1, Pitch Range refers to the range of pitches used to perform a given vocal task. It is usually estimated by measuring the fundamental frequencies (F0) produced during the task, then converting the highest and lowest values to the semitone scale, and expressing the range (difference between highest and lowest) in semitones or octaves. Maximum Loudness refers to the highest sound pressure level produced during a vocal task. It is usually expressed in decibels (dB). Phonation Threshold Pressure refers to the minimum amount of lung air pressure needed to initiate vibration of the phonatory mucosa. It is usually expressed in kPa or cm $H_2O$.

In general, vocal implants, such as vocal hydrogel compositions, that have a lower elastic shear modulus (G') value require lower lung pressure to drive into phonation (with a mucosal wave) and have the potential for a wider range of vocal pitch (F0) variation, but their residence time is shorter thus requiring more frequent injections. Conversely, vocal hydrogels that have a higher elastic shear modulus (G') value require higher lung pressures to drive into phonation (with a mucosal wave) and are potentially limited in terms of vocal pitch (F0) variation, but their residence time is longer thus requiring less frequent injections. An overriding principle in tailoring a vocal implant to a subject is to meet realistic vocal needs/goals while minimizing the number of surgical procedures (injections).

The selection of a specifically formulated vocal hydrogel for a given subject will be based on the following progression of decisions that relate information gathered during the comprehensive voice assessment with biomechanical and residence time characteristics of the candidate hydrogels.

Type of vocal mechanism: Vocal hydrogels with lower G' values (<50 Pa) are better suited to repair of the phonatory mucosa of vocal folds where there is greater potential/need for more pitch variation and vocal control at lower effort/driving pressure than where the phonatory source involves other airway mucosa. Other phonatory mucosal sites (e.g., false cords, corniculate region, aeryepiglottic folds, upper subglottis, pharyngeal mucosa) have limited potential for dynamic variation of vocal parameters such as pitch, and innately require higher driving pressures to vibrate, making them much better suited (e.g., able to tolerate) for hydrogels with higher G' values (>100 Pa). Possible exceptions include esophageal speakers who by swallowing air are limited to using the lower pressures that can be generated by the esophagus to drive a pharyngeal sound source, thus potentially requiring an implant with a lower G'. It is generally advantageous for the latter group to require fewer injections because the injections tend to be more medically involved and the placement of the vocal hydrogel can involve more invasive procedures, depending on the location of the phonatory source (e.g., pharyngeal mucosa for laryngectomy patients).

Vocal needs/goals: the vocal capabilities of subjects who do not use the vocal folds as the primary phonatory source are inherently limited. But among the vast majority of subjects whose phonatory source is the vocal folds, there is a wide range of vocal needs depending on occupation, personality, avocations, etc. At one end of this continuum are the performing voice users (singers and actors) with high vocal demands, who require the production of higher pitches (F0) and the need for more dynamic pitch range and finer control of voice (which requires lower pressures to manipulate). In some embodiments, vocal hydrogels with the lowest G' values (0 to 50 Pa) are best suited to this group. Moreover, this type of person is more likely to accept more frequent injections to maintain their livelihood and/or avocation.

Typical non-performing voice users (most of the population) utilize less range and do not need high levels of vocal control, so they would prefer to maintain their basic ability to carry out daily communication with less frequent injections. Thus, these patients would be prescribed vocal hydrogel compositions that have a G' value in the mid range of approximately 50 to 100 Pa. This group of non-performing voice users can be further differentiated in terms of the amount of voice use required. High voice users (e.g., teachers, trial lawyers) are better treated with vocal hydrogels that have G' values toward the low end of the mid range, because the use of lower driving pressures would less likely contribute to the types of vocal fatigue that can be associated with high levels of voice use (e.g., lecturing). This advantage is balanced against the need to minimize injections by using hydrogels with moderate residence times so as not to overly disrupt the voice user's daily lives. On the other hand, low voice users (e.g., laboratory technicians, retired subjects) could be effectively treated with hydrogels that have G' values toward the upper end of the mid range, because their lower vocal demands place them at lower risk for vocal fatigue and they would benefit from fewer injections.

Degree of vocal deficit: Decisions based on the type of phonatory source and vocal needs of laryngeal (vocal folds) speakers may have to be further adjusted based on the type and degree of vocal deficits that are identified during the comprehensive assessment process. For example, it may be necessary to use hydrogels that have a lower G' than would be initially prescribed if the degree of deficit in vocal pitch (F0) (e.g., pre-treatment pitch of a female is in the male range) or driving pressure (e.g., desire to limit potential increases in driving pressures that are already extremely high) warrant this adjustment.

The mechanical properties (e.g., elastic shear modulus, G' or the viscous shear modulus G" or the swelling ratio) of the vocal hydrogels can be systematically varied to match the desired level of vocal function vs. residence time (e.g., longevity) of the vocal cord repair. Hydrogels with different G' values can be made by varying one or more parameters that include, but are not limited to: the identity, concentration, average molecular weight, and ratio of two (or more) polymers in a precursor solution, the identity and concentration of a photoinitiator, the wavelength and intensity of light used for the polymerization and/or other process parameters such as volume of gels synthesized, time of gelation and incubation, and methods used for shearing the gels (i.e., types and sizes of needles and syringes used for the shearing process).

For example, a gel with G' of about 75 Pa with an expected residence time of about 2 to 4 months can be prepared by the gelation of an aqueous solution that contains PEG-DA and PEG (both made by adding 100 mg polymer to 1 mL buffer) mixed in a volumetric ratio 37:63, respectively, and 0.05% (w/v) Irgacure2959 for 200 s at an UV light intensity of 2 mW/cm$^2$ (measured at 365 nm) using an Omnicure® S2000 Lamp (EXFO Lifesciences, Mississauga, Canada), followed by incubation in pH 7.4 Phosphate buffered saline (PBS) for 24 hours at 37° C. and shearing through needles of decreasing sizes (16, 18, 20, and 22 gauge—twice each).

For example, a gel with G' of about 100 Pa with an expected residence time of about 2 to 4 months can be prepared by the gelation of an aqueous solution that contains PEG-DA and PEG (both made by adding 100 mg polymer to 1 mL buffer) mixed in a volumetric ratio 40:60, respectively, and 0.05% (w/v) Irgacure2959 for 200 s at an UV light intensity of 2 mW/cm$^2$ (measured at 365 nm) using an Omnicure® S2000 Lamp (EXFO Lifesciences, Mississauga, Canada), followed by incubation in pH 7.4 Phosphate buffered saline (PBS) for 24 hours at 37° C. and shearing through needles of decreasing sizes (16, 18, 20, and 22 gauge—twice each).

For example, a gel with G' of about 143 Pa with an expected residence time of greater than 4 months can be prepared by the gelation of an aqueous solution that contains PEG-DA and PEG (both made by adding 100 mg polymer to 1 mL buffer) mixed in a volumetric ratio 43:57, respectively, and 0.05% (w/v) Irgacure2959 for 200 s at an UV light intensity of 2 mW/cm$^2$ (measured at 365 nm) using an Omnicure® S2000 Lamp (EXFO Lifesciences, Mississauga, Canada), followed by incubation in pH 7.4 Phosphate buffered saline (PBS) for 24 hours at 37° C. and shearing through needles of decreasing sizes (16, 18, 20, and 22 gauge—twice each).

For example, a gel with G' of about 25 Pa with an expected residence time of about 1 day to 2 months can be prepared by the gelation of an aqueous solution that contains PEG-DA and PEG (both made by adding 100 mg polymer to 1 mL buffer) mixed in a volumetric ratio 30:70, respectively, and 0.05% (w/v) Irgacure2959 for 200 s at an UV light intensity of 2 mW/cm$^2$ (measured at 365 nm) using an Omnicure® S2000 Lamp (EXFO Lifesciences, Mississauga, Canada), followed by incubation in pH 7.4 Phosphate buffered saline (PBS) for 24 hours at 37° C. and shearing through needles of decreasing sizes (16, 18, 20, and 22 gauge—twice each).

Other gels of different G' (or G" or swelling ratios) and residence times can be prepared by following a similar process, but by changing one or more of the parameters mentioned above. Typically, the ratio of the crosslinkable polymer to the non-crosslinkable in the precursor solution is changed to controllably change G' (or G" or swelling ratio) and residence time. The exact ratio of crosslinkable polymer to the non-crosslinkable polymer needed to produce a gel with required mechanical properties (e.g., G', G", and swelling ratio) may vary depending upon differences in quality of chemicals (e.g., degree of acrylation, polydispersity of the polymers, and impurities), equipment (e.g., light source and incubators) or chemical suppliers used.

Vocal Implants Compositions

Vocal hydrogel compositions, such as PEG hydrogel compositions, can be readily produced with various elastic and viscous shear modulus values (G' and G") that fall within the range that transmit mucosal waves, and have different useful residence times.

Hydrogels are superabsorbent natural or synthetic polymers. Hydrogels can contain up to 99% water by weight. The hydrogel may include one or more polymers. In certain embodiments, the vocal hydrogel composition is a mixture of cross-linked and/or uncross-linked or non-crosslinkable polymers. In particular, semi-interpenetrating networks of polymers that form hydrogels have been found to be useful in the methods of therapy and enhancement described herein. Polymeric hydrogels that are one-component hydrogels have also been found to be useful in the present methods, as long as they have the required minimum and maximum G' and minimum residence times defined herein. Polymeric hydrogels in which two or more components are crosslinked can also be useful in the present methods, as long as they satisfy a required minimum and/or maximum G', and minimum residence times defined herein. In some embodiments, polymeric hydrogels include non-covalent crosslinking bonds, such as ionic crosslinking, hydrogen bonding, or hydrophobic interactions.

In certain embodiments, the hydrogel includes a single polymer. In other embodiments, the hydrogel includes more than one polymer. In some embodiments, the hydrogel includes two polymers. In certain embodiments, the hydrogel includes three, four, five, or more polymers. A mixture of polymers can allow a skilled person to tune the desired characteristics of the hydrogel. Any polymer can be used in preparing a hydrogel. The polymers of the hydrogel can be natural or synthetic. Typically, the polymer(s) used in the hydrogel is at least partially water soluble. Examples of polymers useful in preparing hydrogels include, but are not limited to, polycarbonates (e.g., poly(1,3-dioxan-2one)), polyanhydrides (e.g., poly(sebacic anhydride)), polyhydroxyacids (e.g., poly(β-hydroxyalkanoate)), polypropylfumerates, polycaprolactones, polyamides (e.g., polycaprolactam, polylysine, peptides made with D-amino acids), polyacetals, polyethers, polyesters (e.g., polylactide, polyglycolide), poly(orthoesters), polycyanoacrylates, polyvinyl alcohols, polyurethanes, polyphosphazenes, polyacrylates, polymethacrylates, polyureas, polysaccharides (e.g., hyaluronic acid, dextran, alginate, cellulose), polyamines, and co-polymers thereof. Examples of natural polymers include proteins, peptides (e.g., elastin-like peptide, collagen-mimetic peptides, collagen-related peptides), polysaccharides (e.g., hyaluronic acid, methyl cellulose, dextran, alginate), and nucleic acids.

In certain embodiments, the hydrogel is prepared using a polyol. For example, the hydrogel is prepared using a polyether (e.g., polyethylene glycol, polypropylene glycol, poly(tetramethylene ether)glycol). The hydrogel can include polyethylene glycol. The hydrogel can prepared using a polyether and another type of polymer, a polyethylene glycol and another type of polymer, a polyether and a protein, a polyether and a polysaccharide, a polyether and another polyether, and/or a polyether and a polyol. In some embodiments, the hydrogel is prepared using at least two polyethers. The hydrogel can be prepared using an acrylated version of polyethylene glycol and another type of polymer, such as a diacrylated version of polyethylene glycol and another type of polymer. For example, the hydrogel can be prepared using poly(glycerol sebacate) and acrylated polyethylene glycol, hyaluronic acid and acrylated polyethylene glycol, methyl cellulose and acrylated polyethylene glycol, dextran and acrylated polyethylene glycol, alginate and acrylated polyethylene glycol, polylysine and acrylated polyethylene glycol, poly(glycerol sebacate) and polyethylene glycol-diacrylate, hyaluronic acid and polyethylene glycol-diacrylate, methyl cellulose and polyethylene glycol-diacrylate, and/or dextran and polyethylene glycol-diacrylate. In some embodiments, the hydrogel is prepared using alginate and polyethylene glycol-diacrylate. In certain embodiments, the hydrogel is prepared using polylysine and polyethylene glycol-diacrylate.

In some embodiments, the hydrogel is prepared using a cross-linkable peptide or protein and another type of polymer. For example, the cross-linkable peptide can be a cross-linkable version of elastin-like peptides (ELP), collagen-mimetic peptides (CMP), or collagen-related peptides (CRP). The peptide can include natural L-amino acids, unnatural D-amino acids, or a combination thereof. When a peptide is made from D-amino acids, the resulting peptide is typically less amenable to biodegradation, in particular enzymatic degradation. In some embodiments, the cross-linkable peptide includes an acrylated version of the peptide. Other cross-linkable moieties as described herein can also be used. The cross-linkable peptide can be combined with any other polymer as described herein. For example, the cross-linkable peptide can be cross-linked in the presence of hyaluronic acid, collagen, gelatin, alginate, methyl cellulose, elastin, polylysine, or a derivative thereof. In some embodiments, the hydrogel includes a semi-interpenetrating network of acrylated ELP (D-peptide form) and hyaluronic acid, a semi-interpenetrating network of acrylated ELP (L-peptide form) and hyaluronic acid, a semi-interpenetrating network of acrylated ELP (D-peptide form) and collagen, a semi-interpenetrating network of acrylated ELP (L-peptide form) and collagen, a semi-interpenetrating network of acrylated ELP (D-peptide form) and polylysine, a semi-interpenetrating network of acrylated ELP (L-peptide form) and polylysine, a semi-interpenetrating network of acrylated ELP (D-peptide form) and dextran, a semi-interpenetrating network of acrylated ELP (L-peptide form) and dextran, a semi-interpenetrating network of acrylated ELP (D-peptide form) and alginate, a semi-interpenetrating network of acrylated ELP (L-peptide form) and alginate, a semi-interpenetrating network of acrylated polylysine and hyaluronic acid, a semi-interpenetrating network of acrylated polylysine and dextran, a semi-interpenetrating network of acrylated polylysine and alginate, a semi-interpenetrating network of acrylated polylysine and elastin, a semi-interpenetrating network of acrylated polylysine and collagen, a semi-interpenetrating network of acrylated polylysine and polylysine, and/or a semi-interpenetrating network of acrylated polylysine and gelatin. In some embodiments, the hydrogel includes only natural polymers. In certain embodiments, the hydrogel does not include polyethylene glycol or a derivative thereof.

In some embodiments, the hydrogel is prepared using a cross-linkable polysaccharide and another type of polymer. The cross-linkable polysaccharide can include a water soluble polysaccharide. As an example, the cross-linkable polysaccharide can be a linear polysaccharide or a branched polysaccharide. The hydrogel can include a cross-linkable version of hyaluronic acid, a cross-linkable version of methyl cellulose or other cellulose derivative, a cross-linkable version of dextran, a cross-linkable version of alginate. In some embodiments, the cross-linkable polysaccharide is an acrylated version of a polysaccharide. Other cross-linkable moieties as described herein can also be used. The cross-linkable polysaccharide can be combined with any other polymer as described herein. For example, the cross-linkable polysaccharide can be cross-linked in the presence of hyaluronic acid, collagen, dextran, gelatin, polylysine, alginate, methyl cellulose, elastin, or a derivative thereof. In certain embodiments, the hydrogel includes a semi-interpenetrating network of acrylated methyl cellulose and hyaluronic acid, a semi-interpenetrating network of acrylated methyl cellulose and dextran, a semi-interpenetrating network of acrylated methyl cellulose and alginate, a semi-interpenetrating network of acrylated methyl cellulose and elastin, a semi-interpenetrating network of acrylated methyl cellulose and collagen, a semi-interpenetrating network of acrylated methyl cellulose and polylysine, a semi-interpenetrating network of acrylated methyl cellulose and gelatin, a semi-interpenetrating network of acrylated hyaluronic acid and hyaluronic acid, a semi-interpenetrating network of acrylated hyaluronic acid and dextran, a semi-interpenetrating network of acrylated hyaluronic acid and alginate, a semi-interpenetrating network of acrylated hyaluronic acid and elastin, a semi-interpenetrating network of acrylated hyaluronic acid and collagen, a semi-interpenetrating network of acrylated hyaluronic acid and polylysine, and/or a semi-interpenetrating network of acrylated hyaluronic acid and gelatin. The acrylated hyaluronic acid can be methacrylated hyaluronic acid. In some embodiments, the hydrogel includes a semi-interpenetrating network of acrylated dextran and hyaluronic acid, a semi-interpenetrating network of acrylated dextran and dextran, a semi-interpenetrating network of acrylated dextran and alginate, a semi-interpenetrating network of acrylated dextran and elastin, a semi-interpenetrating network of acrylated dextran and collagen, a semi-interpenetrating network of acrylated dextran and polylysine, a semi-interpenetrating network of acrylated dextran and gelatin, a semi-interpenetrating network of acrylated alginate and hyaluronic acid, a semi-interpenetrating network of acrylated alginate and dextran, a semi-interpenetrating network of acrylated alginate and alginate, a semi-interpenetrating network of acrylated alginate and elastin, a semi-interpenetrating network of acrylated alginate and collagen, a semi-interpenetrating network of acrylated alginate and polylysine, and/or a semi-interpenetrating network of acrylated alginate and gelatin. In some embodiments, the hydrogel includes only natural polymers. In other embodiments, the hydrogel includes only polysaccharides or derivatives of polysaccharides. In certain embodiments, the hydrogel does not include polyethylene glycol or a derivative thereof.

In some embodiments, the hydrogel is prepared using a cross-linkable elastomeric polymer and another type of polymer. For example, the hydrogel can include a cross-linkable version of poly(glycerol sebacate) (PGS). In some embodiments, the cross-linkable polysaccharide can include an acrylated version of an elastomeric polymer. Other cross-linkable moieties as described herein can also be used. The cross-linkable elastomeric polymer can be combined with any other polymer as described herein. The cross-linkable elastomeric polymer can be cross-linked in the presence of hyaluronic acid, collagen, gelatin, alginate, methyl cellulose, elastin, dextran, polylysine, or a derivative thereof. In some embodiments, the cross-linkable elastomeric polymer is cross-linked in the presence of polyethylene glycol, poly(lactic acid), poly (glycolic acid), poly(lactic-co-glycolic acid), or a derivative thereof. In some embodiments, the hydrogel includes a semi-interpenetrating network of acrylated PGS and hyaluronic acid, a semi-interpenetrating network of acrylated PGS and methyl cellulose, a semi-interpenetrating network of acrylated PGS and elastin, a semi-interpenetrating network of acrylated PGS and collagen, a semi-interpenetrating network of acrylated PGS and gelatin, a semi-interpenetrating network of acrylated PGS and dextran, a semi-interpenetrating network of acrylated PGS and alginate, a semi-interpenetrating network of acrylated PGS and polylysine, and/or a semi-interpenetrating network of acrylated PGS and polyethylene glycol (PEG). In some embodiments, the hydrogel includes only natural polymers. In certain embodiments, the hydrogel does not include polyethylene glycol or a derivative thereof.

In some embodiments, the hydrogel is a semi-interpenetrating network of polymers formed when a polymer is crosslinked with itself in the presence of a non-crosslinkable polymer. The crosslinkable polymer can be water soluble. In some embodiments, the non-crosslinkable polymer is water soluble. The water-soluble polymer typically has a minimum solubility of at least approximately 0.1 g of polymer per liter of water. In certain embodiments, the solubility of the polymer in water is at least approximately 0.5 g of polymer per liter of water (e.g., at least approximately 1 g of polymer per liter of water, at least approximately 5 g of polymer per liter of water, or at least approximately 10 g of polymer per liter of water). The hydrogel can also include other polymers, which may be water soluble or not. Any of the polymers described herein may be used to prepare semi-interpenetrating networks of polymers. In certain embodiments, a polyether is used in the preparation of the semi-interpenetrating network of polymers. In some embodiments, a polymer is modified to make it suitable for cross-linking. For example, functional groups suitable for cross-linking (e.g., acrylate moieties, vinyl moieties, alkenyl moieties, alkynyl moieties, methacrylate moieties, cyanoacrylate moieties) may be added to the polymer.

The crosslinkable polymer component of the hydrogel may be any synthetic or natural polymer that is capable of being cross-linked. For example, the cross-linkable polymer can be a synthetic polymer. As another example, the crosslinkable polymer is a natural polymer such as a protein or carbohydrate. The polymer typically will include or may be modified to include functional groups suitable for cross-linking such as acrylates, methacrylates, alkenes, alkynes, carboxylic acids, amines, aldehydes, halides, azides, esters, thiols, diazirines, carbodiimides, imidoesters, azenes, strained rings such as epoxides or aziridines, etc. In certain embodiments, the polymer is an acrylated polyethylene glycol. For example, polyethylene glycol diacrylate, polyethylene glycol triacrylate, etc., may be used as the crosslinkable polymer in the hydrogel. Other polymers besides polyethylene glycol may form the backbone of the polymer. Other exemplary polymer backbones include, but are not limited to, polyesters, polyamines, polyethers, polyamides, polyureas, polyanhydrides, polyhydroxyacids, polypropylfumarates, polycaprolactones, polyacetals, poly(orthoesters), polyvinyl alcohol, polyurethanes, polyphosphazenes, and polycarbonates.

In some embodiments, the polymer backbone is polypropylene glycol. The polymer backbone can be polybutylene glycol. In some embodiments, the polymer is methacrylated rather than acrylated. In certain embodiments, the polymer is cyanoacrylated. In other embodiments, the polymer includes vinyl moieties rather than acrylate or methacrylate moieties. The polymer can include an azide moiety, an epoxide moiety, an aziridine moiety, an amine, an aldehyde, a halogen, an alkenyl moiety, an alkynyl moiety, a carboxylic acid, an ester, a thiol, a diazirine, a carbodiimide, an imidoester, an azene moiety, and/or a nitrene moiety.

The non-crosslinkable polymer component of the hydrogel may also be synthetic or natural. Typically, the non-crosslinkable polymer component of the hydrogel is a water-soluble polymer. In certain embodiments, the non-crosslinkable polymer is a synthetic polymer. In other embodiments, the non-crosslinkable polymer is a natural polymer. Exemplary non-crosslinkable, water soluble polymers include, but are not limited to, polyethers, polypeptides (e.g., polylysine, polyserine, polythreonine, polyglutamate, polyaspartate, polyhistidine, polyarginine), polysaccharides (e.g., alginates, dextran, cellulose, hyaluronic acid), polyamides, proteins (e.g., gelatin, elastin), and derivatives thereof. In certain embodiments, the non-crosslinkable polymer is an analog of the crosslinkable polymer, for example, a non-acrylated polymer (e.g., polyethylene glycol) versus an acrylated polymer (e.g., polyethylene glycol diacrylate).

The physicochemical properties of the hydrogel may be varied by changing the portion of crosslinkable polymer as compared to non-crosslinkable polymer, average molecular weights of either or both polymers, concentration of polymer, and extent of cross-linking.

The average molecular weight (e.g., number average molecular weight) of either polymer may range from approximately 2,000 g/mol up to approximately 600,000 g/mol. For example, the average molecular weight (e.g., number average molecular weight) of the polymers can each independently ranges from approximately 5,000 g/mol to approximately 30,000 g/mol, from approximately 5,000 g/mol to approximately 10,000 g/mol, from approximately 10,000 g/mol to approximately 15,000 g/mol, from approximately 10,000 g/mol to approximately 20,000 g/mol, from approximately 20,000 g/mol to approximately 30,000 g/mol, from approximately 30,000 g/mol to approximately 40,000 g/mol, or from approximately 40,000 g/mol to approximately 50,000 g/mol. In some embodiments, the average molecular weight (e.g., number average molecular weight) of the crosslinkable polymer before cross-linking is approximately 5,000 g/mol, approximately 10,000 g/mol, approximately 15,000 g/mol, approximately 20,000 g/mol, approximately 25,000 g/mol, approximately 30,000 g/mol, approximately 35,000 g/mol, approximately 40,000 g/mol, approximately 45,000 g/mol, or approximately 50,000 g/mol. In certain embodiments, the average molecular weight (e.g., number average molecular weight) of the non-crosslinkable polymer is approximately 5,000 g/mol, approximately 10,000 g/mol, approximately 15,000 g/mol, approximately 20,000 g/mol, approximately 25,000 g/mol, approximately 30,000 g/mol, approximately 35,000 g/mol, approximately 40,000 g/mol, approximately 45,000 g/mol, or approximately 50,000 g/mol. In certain embodiments, the average molecular weight (e.g., number average molecular weight) of either polymer ranges from approximately 50,000 g/mol to approximately 100,000 g/mol, from approximately 100,000 g/mol to approximately 200,000 g/mol, or from approximately 200,000 g/mol to approximately 300,000 g/mol. In certain embodiments, the average molecular weight (e.g., number average molecular weight) of either polymer is approximately 250,000 g/mol. In certain embodiments, the average molecular weight (e.g., number average molecular weight) of either polymer ranges from approximately 300,000 g/mol to approximately 400,000 g/mol, from approximately 400,000 g/mol to approximately 500,000 g/mol, or from approximately 500,000 g/mol to approximately 600,000 g/mol.

Any ratio of crosslinkable to non-crosslinkable polymer may be used in the inventive hydrogels as long as they fall within the range of G' values and residence times defined herein. In certain embodiments, a nearly equal portion of each polymer component is used to prepare the hydrogel. In certain embodiments, the amount of one of the polymers is greater than the other. For example, the amount of the non-crosslinkable polymer can be greater than the amount of the crosslinkable polymer. In certain embodiments, the ratio of non-crosslinkable polymer to crosslinkable polymer is about 10:90, about 20:80, about 30:70, about 40:60, about 50:50, about 60:40, about 70:30, about 80:20, or about 90:10. For example, the ratio of non-crosslinkable polymer to crosslinkable polymer can be about 70:30, about 69:31, about 71:29, about 72:28, or about 65:35. In certain embodiments, the percentage of crosslinkable polymer in the hydrogel ranges from approximately 10% to approximately 50%, from approximately 20% to approximately 40%, or from approximately 25% to approximately 35%. In certain embodiments, the percentage of crosslinkable polymer in the hydrogel is approximately 25%, approximately 30%, approximately 35%, or approximately 40%. In certain embodiments, the percentage of crosslinkable polymer in the hydrogel is approximately 25%, approximately 26%, approximately 27%, approximately 28%, approximately 29%, approximately 30%, approximately 31%, approximately 32%, approximately 33%, approximately 34%, or approximately 35%.

The crosslinkable polymer of the semi-interpenetrating network of polymer is cross-linked via a free radical mediated process. The two or more polymeric components are mixed together in the desired proportion in the hydrogel, and a cross-linking reaction is initiated to cross-link the crosslinkable polymer. In certain embodiments, the polymer is cross-linked using a free radical initiator. The initiator may be a thermal initiator or a photoinitiator. In certain embodiments, the polymer is cross-linked by photo-induced cross-linking (e.g., UV light, visible light, IR light). In certain embodiments, the light is centered at approximately 365 nm. In other embodiments, the polymer is cross-linked by heat (e.g., 30-200° C.). In other embodiments, the polymer is cross-linked using a biological or chemical catalyst. In certain embodiments, the polymers are crosslinked using a molecule that contains multiple (≥2) reactive groups that react with the end-groups on the polymers (e.g., trilysine amine that has 3 amine groups which can be used to crosslink polymers with ester end groups). In certain embodiments, the polymers are cross-linked without using an initiator, i.e., where the polymers have end-groups that spontaneously react with each other (e.g., polymers having esters and amines as end groups).

The cross-linking process is performed under conditions suitable to yield the desired properties of the resulting hydrogel. For example, the extent of cross-linking may be controlled by the time of the reaction, the amount/concentration of initiator, the polymer starting material, the initiator, the frequency of the light used to effect the cross-linking, additives, temperature of the reaction, solvent used, concentration of polymer starting material, oxygen inhibition, water inhibition, etc.

Typically, the initiator decomposes upon heating or exposure to a certain wavelength of light to yield two free radicals that initiate the cross-linking reaction. The initiator may work in a variety of organic solvents, water, or aqueous solutions. Organic solvents that can be used include acetone, ethers, benzene, THF, toluene, hexanes, DMSO, DMF, etc. In certain embodiments, the cross-linking reaction is performed in water or an aqueous solution. In certain particular embodiments, the cross-linking reaction is performed in phosphate-buffered saline solution. The aqueous solution may be acidic or basic.

The initiator is typically chosen based on a variety of concerns including the structure of the polymer, the desired cross-linked material to be produced, the extent of cross-linking, the subsequent use of the material, etc. These and other concerns may be taken into account by one of skill in the art choosing the thermal initiator to be used. The initiator may be obtained from a commercial source such as Sigma-Aldrich, Ciba-Geigy, Sartomer, etc. The initiator may also be prepared synthetically.

In certain embodiments, the initiator is a thermal initiator. Any thermal initiator may be used in the cross-linking reaction. In certain embodiments, the thermal initiator is designed to work at a temperature ranging from 30° C. to 200° C. In certain embodiments, the initiator is designed to work at a temperature ranging from 50° C. to 170° C. In other embodiments, the initiator is designed to work at a temperature ranging from 50° C. to 100° C. In certain embodiments, the initiator is designed to work at a temperature ranging from 100° C. to 170° C. In certain particular embodiments, the initiator is designed to work at approximately 50, 60, 70, 80, 90, 100, 110, 120, 130, 140, 150, 160, or 170° C. The thermal initiators may be peroxides, peracids, peracetates, persulfates, etc. Exemplary thermal initiators include tert-amyl peroxybenzoate; 4,4-azobis(4-cyanovaleric acid); 1,1'-azobis (cyclohexanecarbonitrile); 2,2'-azobisisobutyronitrile (AIBN); benzoyl peroxide; 2,2-bis(tert-butylperoxy)butane; 1,1-bis(tert-butylperoxy)cyclohexane; 2,5-bis(tert-butylperoxy)-2,5-dimethylhexane; 2,5-bis(tert-butylperoxy)-2,5-dimethyl-3-hexyne; bis(1-(tert-butylperoxy)-1-methylethyl)benzene; 1,1-bis(tert-butylperoxy)-3,3,5-trimethylcyclohexane; tert-butyl hydroperoxide; tert-butyl peracetate; tert-butyl peroxide; tert-butyl peroxybenzoate; tert-butylperoxy isopropyl carbonate; cumene hydroperoxide; cyclohexanone peroxide; dicumyl peroxide; lauroyl peroxide; 2,4-pentanedione peroxide; peracetic acid; and potassium persulfate. In certain embodiments, a combination of thermal initiators is used.

In other embodiments, the initiator is a photoinitiator. Photoinitiators produce reactive free radical species that initiate the cross-linking of the cross-linkable component of the hydrogel. Any photoinitiator may be used in the cross-linking reaction. Photoinitiated polymerizations and photoinitiators are discussed in detail in Rabek, Mechanisms of Photophysical Processes and Photochemical Reactions in Polymers, New York: Wiley & Sons, 1987; Fouassier, Photoinitiation, Photopolymerization, and Photocuring, Cincinnati, Ohio: Hanser/Gardner; Fisher et al., "Photoinitiated Polymerization of Biomaterials" Annu. Rev. Mater. Res. 31:171-81, 2001; incorporated herein by reference. The photoinitiator may be designed to produce free radicals at any wavelength of light. In certain embodiments, the photoinitiator is designed to work using UV light (200-400 nm). In certain embodiments, long UV rays are used. In other embodiments, short UV rays are used.

In other embodiments, the photoinitiator is designed to work using visible light (400-800 nm). In certain embodiments, the photoinitiator is designed to work using blue light (420-500 nm). In yet other embodiments, the photoinitiator is designed to work using IR light (800-2500 nm). In certain embodiments, the photoinitiator is a peroxide (e.g., ROOR'). In other embodiments, the photoinitiator is a ketone (e.g., RCOR'). In other embodiments, the compound is an azo compound (e.g., compounds with a —N=N— group). In certain embodiments, the photoinitiator is an acylphosphineoxide. In other embodiments, the photoinitiator is a sulfur-containing compound. In still other embodiments, the initiator is a quinone.

Exemplary photoinitiators include acetophenone; anisoin; anthraquinone; anthraquinone-2-sulfonic acid, sodium salt monohydrate; (benzene) tricarbonylchromium; benzin; benzoin; benzoin ethyl ether; benzoin isobutyl ether; benzoin methyl ether; benzophenone; benzophenone/1-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino) benzophenone; camphorquinone; 2-chlorothioxanthen-9-one; (cumene)cyclopentadienyliron(II) hexafluorophosphate; dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 2,5-dimethylbenzophenone; 3,4-dimethylbenzophenone; diphenyl(2,4,6-trimethylbenzoyl)phosphine oxide/2-hydroxy-2-methylpropiophenone; 4'-ethoxyacetophenone; 2-ethylanthraquinone; ferrocene; 3'-hydroxyacetophenone; 4'-s hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; phenanthrenequinone; 4'-phenoxyacetophenone; thioxanthen-9-one; triarylsulfonium hexafluoroantimonate salts; triarylsulfonium hexafluorophosphate salts; hydrogen peroxide; benzoyl peroxide; benzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizer (Biddle Sawyer); Irgacure 907 (Ciba Geigy); Irgacure 651 (Ciba Geigy); Irgacure 2959 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl)propan-1-one; 1-hydroxycyclohexyl-phenyl-ketone; 2,4,6-trimethylbenzoyldiphenylphosphine oxide; 2-ethylhexyl-4-dimethylaminobenzoate; 2-hydroxy-2-methyl-1-phenyl-1-propanone; 65% (oligo[2-hydroxy-2-methyl-1-[4-(1-methylvinyl)phenyl]propanone] and 35% propoxylated glyceryl triacrylate; benzil dimethyl ketal; benzophenone; blend of benzophenone and α-hydroxy-cyclohexyl-phenyl-ketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional a-hydroxy ketone; ethyl 4-(dimethylamino)benzoate; isopropyl thioxanthone; liquid blend of 4-methylbenzophenone and benzophenone; oligo(2-hydroxy-2 methyl-1-4 (1-methylvinyl)phenyl propanone (emulsion); oligo(2-hydroxy-2-methyl-1-4 (1-methylvinyl)phenyl propanone and 2-hydroxy-2-methyl-1-phenyl-1-propanone (monomeric); oligo (2-hydroxy-2-methyl-1-4 (1-methylvinyl)phenyl propanone and 2-hydroxy-2-methyl-1-phenyl-1-propanone (polymeric); trimethylbenzophenone and methylbenzophenone; and water emulsion of 2,4,6-trimethylbenzoylphosphine oxide, alpha hydroxyketone, trimethylbenzophenone, and 4-methyl benzophenone. In certain embodiments, the photoinitiator is Irgacure 2959. In certain embodiments, a combination of photoinitiators is used.

In some embodiments, the hydrogel is a composition including acrylated polyethylene glycol and polyethylene glycol. The hydrogel can be a composition including polyethylene glycol diacrylate and polyethylene glycol. The number average molecular weight of the polyethylene glycol diacrylate can be approximately 10,000 g/mol. The number average molecular weight of the polyethylene glycol can be approximately 10,000 g/mol. As an example, seven parts of a 10% solution of the non-crosslinkable polymer can be mixed with three parts of a 10% solution of the crosslinkable polymer, and the resulting composition can be cross-linked using a photoinitiator and UV light. In certain embodiments, the photoinitiator Irgacure 2959 (Ciba Specialty Chemicals, Tarrytown, N.J.) is used in the photopolymerization reaction. The intensity of the UV light can range from about 1 mW/cm$^2$ to about 20 mW/cm$^2$ (e.g., about 2 mW/cm$^2$, or about 10 mW/cm$^2$). The resulting hydrogel can be sheared by passing it through needles of decreasing bore size (e.g., 16 gauge, 18 gauge, 20 gauge, and 22 gauge needles). For example, the hydrogel can be passed through each size of needle twice before using a smaller needle.

In some embodiments, the hydrogel is a composition including acrylated polyethylene glycol and hyaluronic acid. The hydrogel can be a composition including polyethylene glycol diacrylate and hyaluronic acid. The number average molecular weight of the polyethylene glycol diacrylate can be approximately 10,000 g/mol. The number average molecular weight of the hyaluronic acid can be approximately 560,000 g/mol. As an example, 73 parts of a 1 mg/mL solution of the hyaluronic acid can be mixed with 27 parts of a 100 mg/mL of the crosslinkable polymer, and the resulting composition can cross-linked using a photoinitiator and UV light. In certain embodiments, the photoinitiator Irgacure 2959 (Ciba Specialty Chemicals, Tarrytown, N.J.) is used in the photopolymerization reaction. The intensity of the UV light can range from about 0.5 mW/cm$^2$ to about 20 mW/cm$^2$ (e.g., from about 1 mW/cm$^2$ to about 5 mW/cm$^2$, from about 5 mW/cm$^2$ to about 10 mW/cm$^2$, about 1 mW/cm$^2$, about 2 mW/cm$^2$, about 5 mW/cm$^2$, or about 10 mW/cm$^2$). The resulting hydrogel can be sheared by passing it through needles of decreasing bore size (e.g., 16 gauge, 18 gauge, 20 gauge, and 22 gauge needles). For example, the hydrogel can be passed through each size of needle twice before using a smaller needle.

In some embodiments, the hydrogel is a composition including acrylated polyethylene glycol and dextran. For example, the hydrogel can be a composition including polyethylene glycol diacrylate and dextran. The number average molecular weight of the polyethylene glycol diacrylate can be approximately 10,000 g/mol. The number average molecular weight of the dextran can be approximately 200,000 g/mol. As an example, seven parts of a 20 mg/mL solution of the dextran can be mixed with three parts of a 100 mg/mL of the crosslinkable polymer, and the resulting composition can be cross-linked using a photoinitiator and UV light. In certain embodiments, the photoinitiator Irgacure 2959 (Ciba Specialty Chemicals, Tarrytown, N.J.) is used in the photopolymerization reaction. The intensity of the UV light can ranges from about 1 mW/cm$^2$ to about 20 mW/cm$^2$ (e.g., about 2 mW/cm$^2$, or about 10 mW/cm$^2$). The resulting hydrogel can be sheared by passing it through needles of decreasing bore size (e.g., 16 gauge, 18 gauge, 20 gauge, and 22 gauge needles). For example, the hydrogel is passed through each size of needle twice before using a smaller needle.

In some embodiments, the vocal implant is a gel resulting from the crosslinking of polymer chains containing two or more complementary reactive groups. The complementary reactive groups on the polymer(s) can be an electrophile and a nucleophile. For example, the complementary reactive groups on the polymer(s) can include an ester and an amine, a thiol (sulfahydryl) and an acrylate, a thiol and a thiol, an acrylate and an amine, a carboxylic acid and an amine, and/or an azide and an alkyne. In some embodiments, ester derivative of polyethylene glycol is crosslinked with an amine derivative of polyethylene glycol. In other embodiments, thiol derivatives of polyethylene glycol are used to crosslink with acrylated derivatives of polyethylene glycol.

In some embodiments, a small-molecule cross-linker molecule with a reactive group is used to crosslink polymer(s) with the complementary reactive groups. For example, complementary reactive groups on the polymers and the small molecule crosslinker can include an ester and an amine, a thiol (sulfahydryl) and an acrylate, a thiol and a thiol, an acrylate and an amine, a carboxylic acid and an amine, and/or an azide and an alkyne. As an example, trilysine amine can be used to crosslink an ester derivative of polyethylene glycol.

The vocal implant can be a thermosensitive (or thermoresponsive) polymer(s) that gels at the temperature of the injection site. For example, the thermoresponsive polymer can include poly-N-isopropyl acrylamide (pNIPAM), poloxamers, poloxamines, copolymers of polyethylene glycol and poly-L-lactide-co-glycolide, and derivatives thereof.

The vocal implant can be formed in situ at the injection site or pre-formed outside the body and then implanted at the required site.

Although the descriptions of hydrogel compositions provided herein are principally directed to compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the disclosure is contemplated include, but are not limited to, humans and/or other primates; mammals, including mammals such as cattle, pigs, horses, sheep, cats, ferrets, and/or canines.

The formulations of the pharmaceutical compositions described herein may be prepared by any method known or hereafter developed in the art of pharmaceutics. In general, such preparatory methods include the step of bringing the hydrogel into association with one or more excipients and/or one or more other accessory ingredients, and then, if necessary and/or desirable, shaping, and/or packaging the product into a desired single- or multi-dose unit.

The relative amounts of the hydrogel, the pharmaceutically acceptable excipient(s), and/or any additional ingredients in a pharmaceutical composition of the disclosure will vary, depending upon the identity, size, and/or condition of the subject. By way of example, the composition may include between 1% and 99% (w/w) of the hydrogel.

Pharmaceutical formulations of the present disclosure may additionally include a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of the hydrogel compositions include, but are not limited to, inert diluents, dispersing agents, surface active agents and/or emulsifiers, disintegrating agents, preservatives, buffering agents, lubricating agents, and/or oils. Such excipients may optionally be included in the inventive formulations. Excipients such as coloring agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g., polyoxyethylene monostearate [Myrj®45], polyoxyethylene hydrogenated castor oil, polyethoxylated castor oil, polyoxymethylene stearate, and Solutol), sucrose fatty acid esters, polyethylene glycol fatty acid esters (e.g., Cremophor®), polyoxyethylene ethers, (e.g., polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for parenteral administration include, but are not limited to, pharmaceutically acceptable emulsions, microemulsions, solutions, suspensions, syrups, and elixirs. In addition to the hydrogel, the liquid dosage forms may include inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments, the hydrogel of the disclosure is mixed with solubilizing agents such as Cremophor®, alcohols, oils, modified oils, glycols, polysorbates, cyclodextrins, polymers, and combinations thereof. Injectable formulations, for example, sterile injectable aqueous or oleaginous suspensions, may be formulated according to the known art using suitable dispersing or wetting agents and suspending agents. A sterile injectable preparation may be a sterile injectable solution, suspension, or emulsion in a non-toxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

General considerations in the formulation and/or manufacture of pharmaceutical agents may be found, for example, in *Remington: The Science and Practice of Pharmacy* $21^{st}$ ed., Lippincott Williams & Wilkins, 2005.

In some embodiments, the vocal implants, e.g., hydrogel compositions, can include biologically active agents in the form of nanoparticles and nanocrystals, generally having a particles size of less than about 500 nm, optionally less than about 300 nm, and in some aspects, less than 100 nm. Useful non-limiting active agents in the form of nanoparticles include magnesium oxide, and metal based nanoparticles, including gold, silver, and the like. In some embodiments, the vocal implants, e.g., hydrogel compositions, can include biologically active agents in the form of microparticles and microspheres, generally having a particles size of less than about 500 micron, optionally less than about 100 micron, and in some aspects, less than 10 micron. Useful non-limiting active agents in the form of microparticles and microspheres include degradable microspheres of poly-L-lactide-co-glycolide (PLGA), polylactide (PLA), polyanhydrides and the like. Suitable, non-limiting examples of active agents in the form of drugs include 5-Fluorouracil (5-FU): an anti-metabolite drug commonly used in cancer treatment. Suitable chemotherapeutic drugs can be divided into the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleevec® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX), irinotecan, topotecan, amsacrine, etoposide, etoposide phosphate, teniposide, dactinomycin, and monoclonal antibodies, such as trastuzumab (Herceptin®), cetuximab, bevacizumab and rituximab (Rituxan®), among others.

Other examples of therapeutic moieties include, but are not limited to, antimicrobial agents, analgesics, antiinflammatory agents, counterirritants, coagulation modifying agents, electrolytes, muscle relaxants, anticonvulsants, contrast materials, radiopharmaceuticals, antiallergic agents, antiviral agents, and antineoplastic or cytostatic agents or other agents with anticancer properties, or a combination thereof. Other examples include antiinfectives such as antibiotics and antiviral agents; analgesics and analgesic combinations; and naturally derived or genetically engineered proteins, polysaccharides, glycoproteins, or lipoproteins. Other active agents in the form of therapeutic agents are described in PCT WO 2008/124632, which is incorporated herein by reference in its entirety.

In some embodiments, the vocal implants, e.g., hydrogel compositions, can include non-genetic therapeutic agents such as: (a) anti-inflammatory agents such as dexamethasone, prednisolone, corticosterone, budesonide, estrogen, sulfasalazine and mesalamine; (b) antineoplastic/antiproliferative/anti-mitotic agents such as paclitaxel, 5-fluorouracil, cisplatin, vinblastine, vincristine, epothilones, endostatin, angiostatin, angiopeptin, monoclonal antibodies, thymidine kinase inhibitors, inhibitors of HSP 90 protein (i.e., Heat Shock Protein, which is a molecular chaperone or housekeeping protein and is needed for the stability and function of other client proteins/signal transduction proteins responsible for growth and survival of cells including geldanamycin; (c) anesthetic agents such as lidocaine, bupivacaine and ropivacaine; (d) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (e) protein kinase and tyrosine kinase inhibitors (e.g., tyrphostins, genistein, quinoxalines); (f) antimicrobial agents such as triclosan, cephalosporins, antimicrobial peptides such as magainins, aminoglycosides and nitrofurantoin; (g) cytotoxic agents, cytostatic agents and cell proliferation affectors such as growth factors, e.g., fibroblast growth factors (FGF), nerve growth factors (NGF), transforming growth factors (TGF), such as TGF alpha and TGF beta, and vascular endothelial growth factor (VEGF); (h) inhibitors of leukocyte recruitment, such as monoclonal antibodies; (l) cytokines; (m) hormones; and/or (n) immune response modifiers including aminoquizolines, for instance, imidazoquinolines such as resiquimod and imiquimod.

In some embodiments, the vocal implants, e.g., hydrogel compositions, can include therapeutic drugs, which by way of non-limiting example includes chemotherapeutic drugs, such as doxorubicin (molecular mass of about 543.5 g/mol); paclitaxel or Taxol™ (molecular mass of about 853.9 g/mol), cholesterol lowering drug, lovastatin (molecular mass of about 404.5 g/mol), NSAID analgesic ibuprofen (molecular mass of 206.3 g/mol). Other active agents include macromolecules, which include a wide range of compounds, generally including polymers and biomolecules having relatively large molecular weights. Such macromolecules can be naturally occurring or synthesized. A variety of polymers well known to those of skill in the art can be employed if the polymers are smaller than the core structure in which they are distributed. Amino acids, peptides (amino acids linked via peptide bonds); polypeptides (linear chains of peptides); and proteins (primary, secondary, and tertiary folded polypeptides) are all contemplated as active agents. Exemplary active agent proteins include heat shock protein 70 (HSP70) for dendritic cells and folic acid for cancer cells. Exemplary toxins for use as active agents include saporin and Botulinum toxins. Exemplary sugars include silylic acid leukocytes and glucuronic acid, for example.

A wide variety of cells can be appropriate for use in accordance with the vocal implant, e.g., vocal hydrogel compositions, described herein, as will be readily appreciated by one of skill in the art of cell implantation. For example, cells for use in connection with the implants include cells of human origin (autologous or allogeneic), including progenitor cells (e.g., endothelial progenitor cells), stem cells (e.g., mesenchymal), adipose-derived stem cells, pluripotent stem cells, fibroblasts (e.g., vocal fold fibroblasts, skin fibroblasts, or other mammalian fibroblasts), pericytes, or from an animal, bacterial, or fungal source (xenogeneic), which can be genetically engineered, if desired, to deliver proteins or hormones of interest.

Exemplary genetic therapeutic agents for use in connection with the implants include anti-sense DNA and RNA as well as DNA coding for: (a) anti-sense RNA; (b) tRNA or rRNA to replace defective or deficient endogenous molecules; (c) angiogenic factors including growth factors such as acidic and basic fibroblast growth factors, epidermal growth factor, transforming growth factor α and β, platelet-derived endothelial growth factor, platelet-derived growth factor, and tumor necrosis factor α (d) cell cycle inhibitors; and (e) thymidine kinase ("TK") and other agents useful for interfering with cell proliferation.

In some embodiments, vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Methods of Making Vocal Implant Compositions

Figure 2:
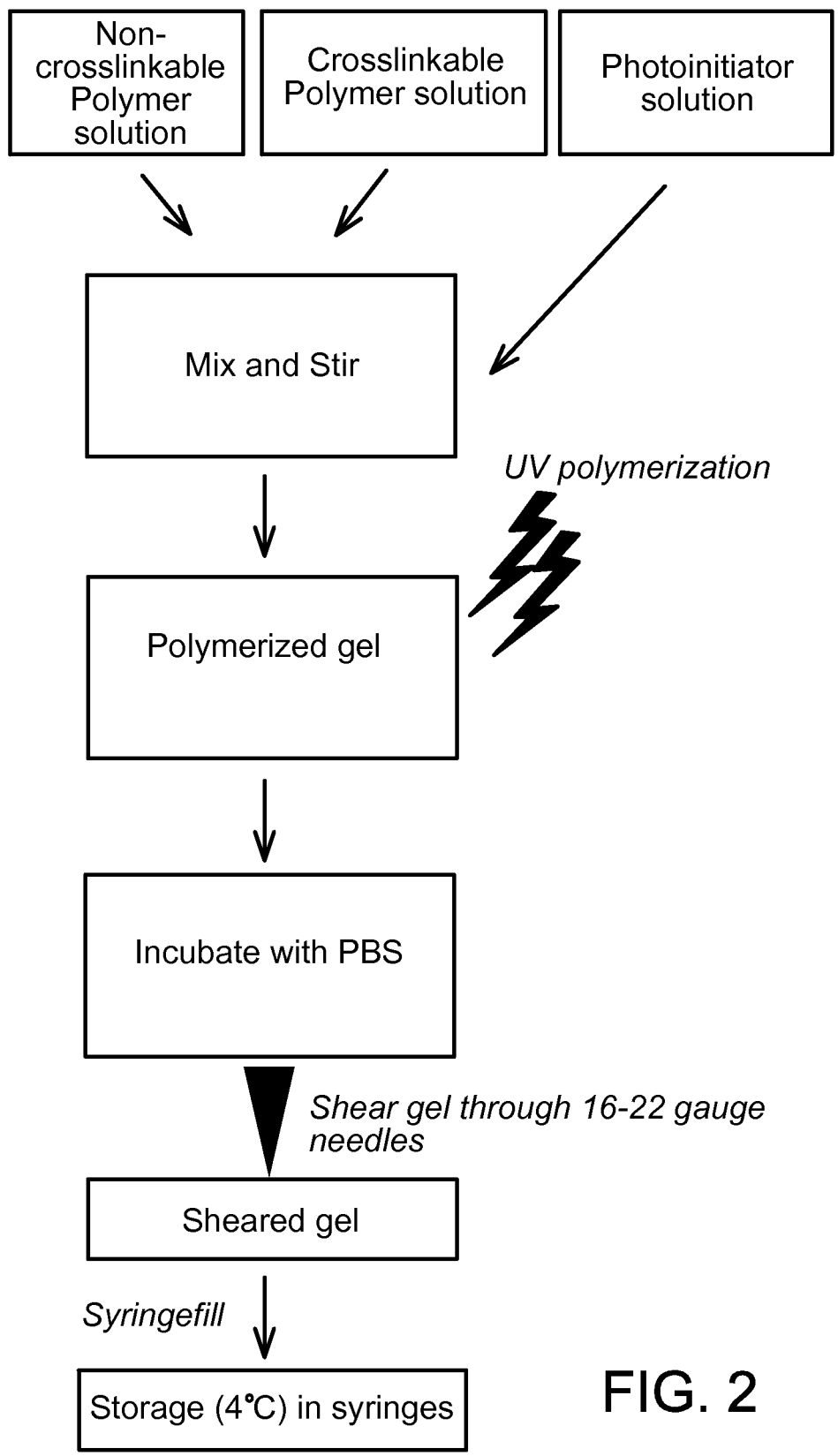
FIG. 2 is a flow chart of an embodiment of a method of making a hydrogel.

In general, referring to FIG. 2, the gel compositions with well-defined chemical and physical properties can be made using polymerization, e.g., UV light-catalyzed polymerization. Uniform polymerization can be ensured by careful control of various parameters that include but are not limited to, e.g., volume (container size), (UV) light intensity, light source, photoinitiator concentration, mixing of precursor solution before and during gelation, and distance from the light source Following polymerization and swelling, the gels are sheared to produce the final product that has the desired G' and G" values as well as the desired residence time after implantation. Shearing is typically done by forcing the hydrogel through a narrowed opening. In certain embodiments, smaller and smaller openings may be used. In certain embodiments, the hydrogel is forced through a series of needles with smaller and smaller bores. For example, the hydrogel may be passed successively through 16 gauge, 18 gauge, 20 gauge, and 22 gauge needles. In certain embodiments, a syringe-like device that can contain a larger volume is used. In other embodiments, ultrasonic and/or mechanical shearing methods may be used. In certain embodiments, a homogenizer is used. In certain embodiments, a microfluidizer is used. The hydrogel is typically processed until the desired elastic shear modulus of the material is achieved.

The hydrogel can be optionally purified and/or otherwise processed after it has been prepared.

Aqueous solutions of non-crosslinkable polymer, e.g., PEG, and the crosslinkable polymer, e.g., PEG-DA, can be made in a buffer, e.g., PBS buffer, at concentrations varying from 0.1 mg/ml to 500 mg/ml (e.g., from 10 to 500 mg/ml, from 100 to 500 mg/ml, from 100 mg to 200 mg/ml, from 200 to 500 mg/ml, from 200 to 400 mg/ml, from 200 to 300 mg/ml, 10 mg/ml, 100 mg/ml, 200 mg/ml, etc.). For example, to make 100 mg/mL of the polymer solution, 100 mg of the polymer is added to 1 mL of buffer. The number average molecular weights of both the polymers can be same or different, e.g., number average molecular weights for the PEG and PEG-DA could vary from 100 Da to 50,000 Da (e.g., 3400 Da, 10,000 Da, 20,000 Da, etc.). The concentrations of both polymers can be the same or different, e.g., concentrations of both the polymers can be 100 mg/ml or it can be 100 mg/ml for the crosslinkable polymer and 20 mg/ml for the non-crosslinkable polymer. Other polymers such as hyaluronic acid, dextran, or alginate, and their crosslinkable or other derivatives can also be used in place of or along with PEG or PEG-DA. If other polymers are used, then the concentrations of the polymers can vary from 0.1 mg/mL to 500 mg/mL (e.g., from 10 to 500 mg/ml, from 100 to 500 mg/ml, from 100 mg to 200 mg/ml, from 200 to 500 mg/ml, from 200 to 400 mg/ml, from 200 to 300 mg/ml, 0.1 mg/mL, 0.5 mg/mL, 20 mg/mL, 500 mg/mL etc.) and the molecular weights of the polymers can vary from 1000 Da to >2,000,000 Da (e.g., from 2 to 2000 kDa, from 5 to 2000 kDa, from 10 to 1000 kDa, from 100 to 500 kDa, 200,000 Da, 560,000 Da, etc.).

The aqueous solutions can then mixed in a predetermined volumetric ratio of the crosslinkable polymer:non-crosslinkable polymer (e.g., 10:0, 5:5, 3:7, etc). The precursor solution (1 ml) is gelled for 10 seconds to 30 minutes (e.g., for 200 seconds, 10 min, 20 minutes, or 25 minutes), using a photoinitiator such as Irgacure® 2959 (Ciba, Tarrytown, N.Y.) at concentrations ranging from 0.01% to 0.5% (w/v) (e.g., 0.05%). An Omnicure® S2000® lamp (EXFO Lifesciences, Mississauga, Canada) or any other comparable UV light source that generates ultra-violet light of intensity 1 mW/cm$^2$ to 20 mW/cm$^2$ (e.g., 2 mW/cm$^2$, 3 mW/cm$^2$, 10 mW/cm$^2$ etc.) (measured at 365 nm) is used for the gelation. The process may be modified to prepare large amounts (>1 mL) of gels with similar physicochemical properties.

Post-gelation, the gels can be incubated in excess PBS (e.g., about 9 times the volume of the gel) for 12 to 72 hours (e.g., 12 to 72 hours, 12 to 48 hours, 24 to 48 hours, 24 hours, or 48 hours) at 37° C.

To achieve the desired elastic shear modulus (G'), the swollen gels can be progressively sheared. Shearing is typically done by forcing the hydrogel through a narrowed opening. For example, the gel can be forced through needles of decreasing bore size to make them ultimately injectable through a small gauge needle, e.g., a 25-gauge needle. In certain embodiments, increasingly smaller openings may be used. For example, the hydrogel can be passed successively through 16 gauge, 18 gauge, 20 gauge, and 22 gauge needles. In some embodiments, a syringe-like device that can contain a larger volume is used. In other embodiments, ultrasonic and/or mechanical shearing methods can be used. In certain embodiments, a homogenizer is used. In certain embodiments, a microfluidizer is used.

The viscoelastic shear properties (G', G", intrinsic viscosity) of all of the hydrogels are measured at 37° C. and low frequencies (1 Hz to 10 Hz) using an AR-2000 rheometer (TA Instruments, Inc., New Castle, Del.). A cone-and-plate geometry is used to apply oscillatory shear to the gel samples using an acrylic cone (60 mm diameter, 2° angle) and a flat metallic peltier plate heated to 37° C. The hydrogels are placed between the heated plate and the cone so that a manufacturer-specified gap of 61 μm is maintained between the cone and the plate. The hydrogels are subjected to an oscillatory shear at 1

Hz for 2 minutes to equilibrate the entire hydrogel to a uniform temperature of 37° C. Strain sweep tests are done to ensure that the shear property measurements are done in the linear region of the stress-strain curve.

The viscoelastic shear properties are independent of the percentage strain in the linear region. A target shear strain value is therefore identified by measuring the viscoelastic shear properties as a function of percentage strain applied (0.6% strain is typically used to measure the shear properties using a frequency sweep). Measurements of the shear properties are then made by systematically varying the frequency from 1 to 10 Hz. The elastic shear modulus (G') and viscous shear modulus (G") at 10 Hz and 37° C. are used as a measure of the mechanical properties of the gels.

The selected vocal implant composition can be packaged into 0.5 to 5 mL plastic syringes and capped/sealed. If the vocal implant is not a hydrogel, it can be stored in a receptacle, such as a pouch, to keep it sterile. Syringes and pouches should meet specific pull strengths and burst test requirement. Implantation into a subject (e.g., an animal, a human) can be done in the operating room by means of general anesthesia and direct laryngoscopy or pharyngoscopy, or with local-regional anesthesia with flexible or telescopic viewing of the implant site. The latter is typically done in a doctor's office without sedation.

Implantation—General Anesthesia

After obtaining good general endotracheal anesthesia with the intubation being done by a surgeon, the patient can be prepped and draped in the usual fashion. A Universal Modular Glottiscope (Zeitels, S. M., *A Universal Modular Glottiscope System: The Evolution of a Century of Design and Technique for Direct Laryngoscopy*. Annals of Otology, Rhinology and Laryngology, 1999. 108(Supplement 179): p. 1-24; Zeitels, S. M., Universal Modular Laryngoscope/Glottiscope System. U.S. Pat. No. 5,893,830) can be used to visualize the entirety of the glottis. The patient can be placed in Jackson position (Jackson, C., *Position of the Patient for Peroral Endoscopy, in Peroral Endoscopy and Laryngeal Surgery*. 1915, Laryngoscope Co.: St. Louis. p. 77-88) and maintained with gallows to achieve elevated-vector-suspension. Zeitels, S. M., *Premalignant epithelium and microinvasive cancer of the vocal-fold: The evolution of phonomicrosurgical management*. Laryngoscope, 1995. 105(Supplement 67): p. 1-51; Zeitels, S. M., Burns, J. A., Dailey, S. H., *Suspension laryngoscopy revisited*. Annals of Otology, Rhinology, & Laryngology, 2004. 113(1): p. 16-22. External counter-pressure can be applied with silk tape. Brunings, W., *Direct Laryngoscopy: Autoscopy by Counter-pressure, in Direct laryngoscopy, Bronchoscopy, and Esophagoscopy*. 1912, Bailliere, Tindall, & Cox: London. p. 110-115; Zeitels, S. M., Vaughan, C. W., *"External Counter-Pressure" and "Internal Distension" for Optimal Laryngoscopic Exposure of the Anterior Glottal Commissure*. Annals of Otology, Rhinology & Laryngology, 1994. 103: p. 669-675. A surgical microscope can be used to examine the glottis and perform the procedure at the highest magnification, which is 13× for the 400 mm focal length that is used. Scalco, A. N., Shipman, W. F., Tabb, H. G., *Microscopic Suspension Laryngoscopy*. Annals of Otology, Rhinology, & Laryngology, 1960. 69: p. 1134-1138

A 5 mm right-angle blunt probe can be placed alongside the vocal fold to be treated for size calibration. A specially-designed vocal-fold infusion needle (e.g., a 25 gauge Zeitels Vocal-fold Infusion needle (Endocraft®, LLC, Providence, R.I.) (Kass, E. S., Hillman, R. E., Zeitels, S. M., *The Submucosal Infusion Technique in Phonomicrosurgery*. Annals of Otology, Rhinology, & Laryngology, 1996. 105: p. 341-347; Zeitels, S. M., Vaughan, C. W., *A submucosal vocal-fold infusion needle*. Otolaryngology: Head and Neck Surgery, 1991. 105: p. 478-479) can be used to perform a subepithelial injection of approximately 0.1 to 0.5 cc under or into the SLP of the selected vocal hydrogel composition in the region of diminished pliability. After the injection is done, the larynx can be sprayed with topical 4% plain lidocaine to avoid laryngospasm during emergence from anesthesia. The patient can then be taken out of suspension and the laryngoscope can be removed. Subsequently he/she can be awakened in the operation room and extubated, and then sent to the recovery room for standard observation and release.

Implantation—Local and/or Regional Anesthesia

The patient can be prepped and draped in the usual fashion and seated in an upright position with the head extended at the alto-occipital joint and flexion of the cervical spine. Cetacaine can be topically applied to the oral cavity and the oropharynx and 2% lidocaine nebulized to laryngopharynx and larynx. Using the Ford syringe (Xomed Inc., Jacksonville, Fla.), approximately 1.5 cc of topical 2% plain lidocaine can be dripped over the injection site. If the procedure is done transorally with telescopic control, the Ford injector and needle can be used to perform a subepithelial injection of 0.1 cc to 0.5 cc of the vocal biomaterial composition in the region of diminished pliability. If the procedure is done transcervically, transnasal flexible laryngoscopy can be used to view the injection site. In addition to topical anesthesia of the larynx and pharynx, local anesthesia with 2% plain lidocaine with 0.05% oxymetazoline can be used to anesthetize the nasal passage. Once there is adequate anesthesia, the flexible laryngoscope can be passed to visualize the pathology. The anterior neck skin over the thyroid notch can be anesthetized with 2% lidocaine with 1/100,000 epinephrine (3 cc). Then a 25 gauge spinal needle can pass through the infrapetiole region of the supraglottis. Under flexible laryngoscopic control, 0.1 cc to 0.5 cc of the vocal implant composition can be injected in the region of diminished pliability.

Larger volume injections of the vocal implant can be required for supraglottal, upper subglottal and pharyngeal phonatory sound source locations.

Kits

This disclosure also provides packages or kits, including one or more vocal implants, e.g., vocal hydrogel compositions or vocal hydrogel components as described herein in a container. For example, the container may include a hydrogel composition ready for use in a patient. Or the containers may contain the components of the hydrogel (e.g., crosslinkable polymer(s), non-crosslinkable polymer(s), initiators, catalysts, etc.) which must be mixed and cross-linked to form the hydrogel. The package can also include a notice associated with the container, typically in a form prescribed by a government agency regulating the manufacture, use, or sale of medical devices and/or pharmaceuticals, whereby the notice is reflective of approval by the agency of the compositions, for human or veterinary administration to treat vocal cord disease or other soft tissue repair or augmentation. Instructions for the use of the hydrogel composition may also be included. Such instructions may include information relating to administration of the hydrogel to a patient. In particular, the instructions may include information regarding the injection of the hydrogel into the vocal cords of patient.

In certain embodiments of the disclosure the kit will include multiple individual containers, each containing a component of the hydrogel. For example, a first container may contain a crosslinkable polymer, and a second container may contain a non-crosslinkable polymer. The cross-linking initiator may be provided in yet a third container. The polymers may be provided in predetermined amounts such that when mixed with each other in solution in the presence of an initiator they form a hydrogel having the desired characteristics. The package may also include one or more containers containing biologically active agent(s) to be included in the hydrogel prior to administration.

The package may include a device or receptacle for preparation of a hydrogel composition. The device may be, e.g., a measuring or mixing device.

The package may also optionally include a device for administering a hydrogel composition of the disclosure. Exemplary devices include specialized syringes, needles (e.g., a Ford Injection Needle: Xomed Inc., Jacksonville, Fla. or a Zeitels Vocal-Fold Infusion needle: Endocraft®, LLC, Providence, R.I.), and catheters that are compatible with a variety of laryngoscope designs.

The components of the kit may be provided in a single larger container, e.g., a plastic or styrofoam box, in relatively close confinement. Typically, the kit is conveniently packaged for use by a health care professional. In certain embodiments, the components of the kit are sterilely packaged for use in a sterile environment such as an operating room or physician's office.

EXAMPLES

The invention is further described in the following examples, which do not limit the scope of the invention described in the claims.

Example 1

Calf Larynx Ex-Vivo Model

Figure 3:
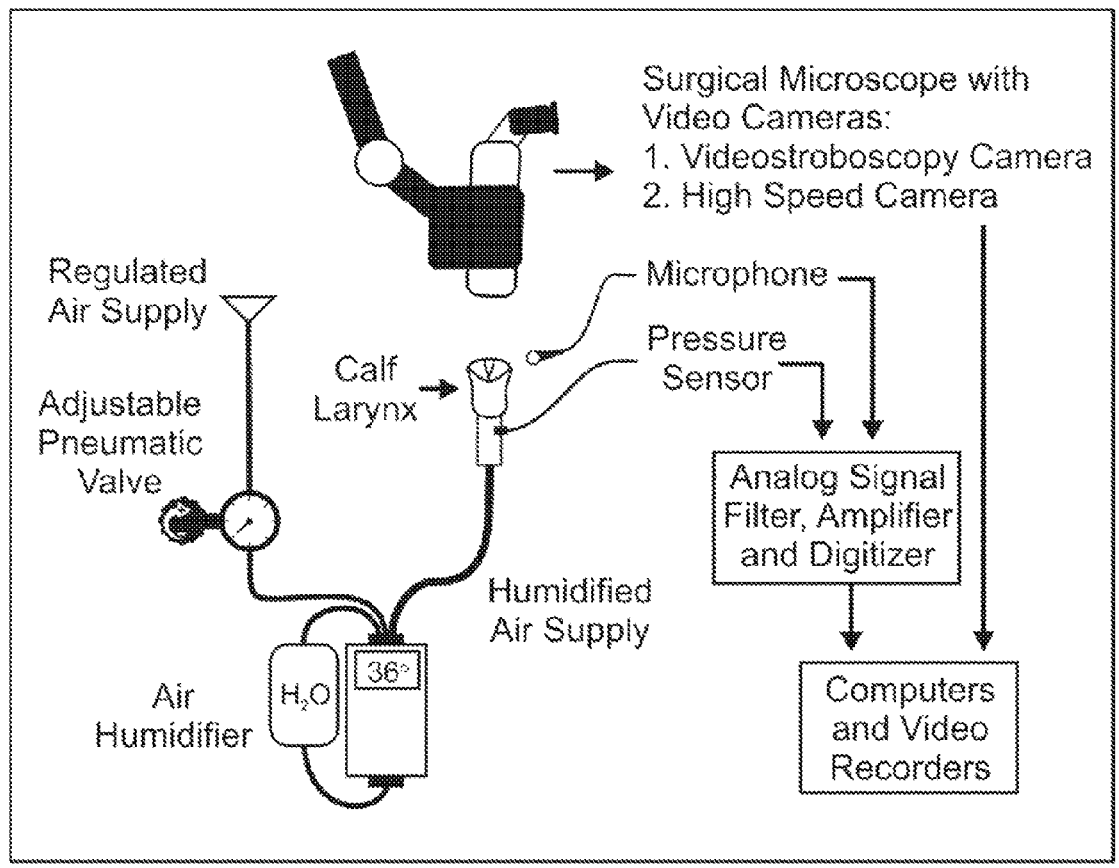
FIG. 3 is a schematic representation of an ex vivo calf larynx model.

The calf larynx was chosen to prepare a reliable and repeatable ex-vivo model for accurate mechanical testing of injectable gels due to similarities between adult human and calf larynges in vocal fold length, size, and subglottic airway shape, thereby providing a good indication of how human vocal folds would vibrate after injection of these tested materials. Larynges were obtained within 0 to 3 days of calf slaughter, maintained at 4° C. and were tested within 0 to 3 days after excision. The set-up used for carrying out the testing is shown in FIG. 3.

Figure 4A:
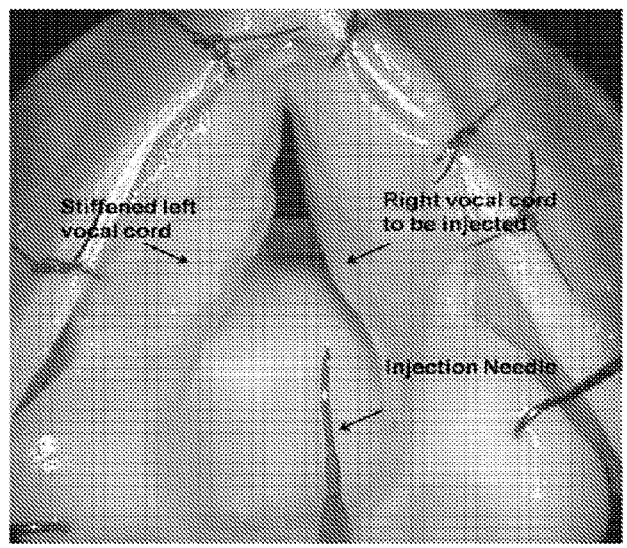
FIGS. 4A to 4C are a series of photographic representations of an ex vivo calf vocal cord model used to test different hydrogel compositions.

Prior to testing each material, the recipient larynx was warmed to room temperature from cold storage. The supraglottic tissues approximately 1 cm above the vocal folds were removed to provide access to, and visibility of, the vocal folds. Multiple sutures were placed through the cut supraglottic airway lateral and anterior to the vocal folds to draw the soft tissues and thyroid cartilage together and away from the vocal folds, preventing these tissues from impeding vocal fold vibration or blocking visibility of the glottis. Referring to FIG. 4A, approximately 5 cm of upper trachea remained attached to the larynx which served as means of mounting the larynx onto a tube providing subglottic air flow, whereas the remainder of the inferior trachea was removed.

The left vocal fold was injected throughout the superficial and deep paraglottic region and supraglottic region with approximately 0.4 mL of cyanoacrylate adhesive (Loctite Superglue) to stiffen the tissues and provide a rigid surface against which the contralateral vocal fold could vibrate in a consistent and controlled manner. The right vocal fold was likewise stiffened with cyanoacrylate adhesive, but using approximately 0.2 ml restricted to the deep paraglottic and supraglottic regions, leaving the medial superficial region pliable for receiving gel injection.

The right vocal fold was driven into entrained oscillation with a delivered subglottic air flow both before and after gel injection. Subglottic air flow was delivered using regulated and pressurized air controlled using an adjustable valve. Subglottic air was heated and humidified to approximately 37° C. using a ConchaTherm® unit (High-Flow Model; Hudson RCI, Temecula, Calif.) to prevent laryngeal tissues from becoming dry during testing. The air supply tubing from the humidification unit lead to a rigid plastic tube ~1.5 cm in diameter and 10 cm long, held by a variable friction arm (Manfroto model 143N, Italy) at a comfortable working distance in front of a Leica® F40 surgical microscope.

Referring to FIG. 3, each larynx was mounted to the air supply system for testing by sliding the subglottic trachea onto the rigid plastic tube (see FIG. 3) and forming an air-tight seal with nylon tie wraps. A pressure sensor (MPX2010GP; Motorola, Schaumburg, Ill.) was mounted on the rigid air supply tube near its connection to the trachea in order to monitor subglottic pressures delivered during larynx testing. A condenser microphone (ECM-50PSW; Sony, New York, N.Y.) was positioned approximately 7 cm lateral to the vocal folds. Audio recordings were calibrated by creating a simulated glottal sound source at the glottis (Cooper-Rand Electrolarynx) and measuring the resulting sound amplitude at the microphone using a sound pressure meter (Rion NL-20). Simultaneous acoustic and pressure signals were filtered and recorded digitally (20,000 Hz sampling rate) with Axon Instruments hardware (Cyberamp 380, Digidata 1440a) and software (Axon Instruments). Phonation threshold pressures (PTP) were monitored in real-time during data collection in order to monitor and control phonation driving pressures, and were also measured from recorded signals during subsequent analyses.

Figure 4B:
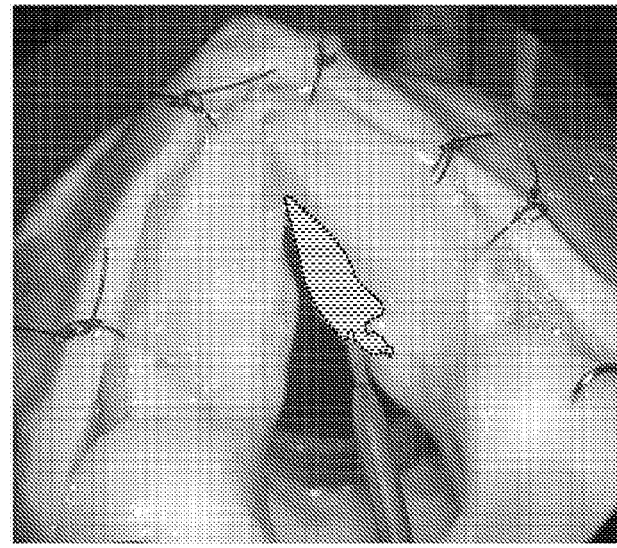
Figure 4C:
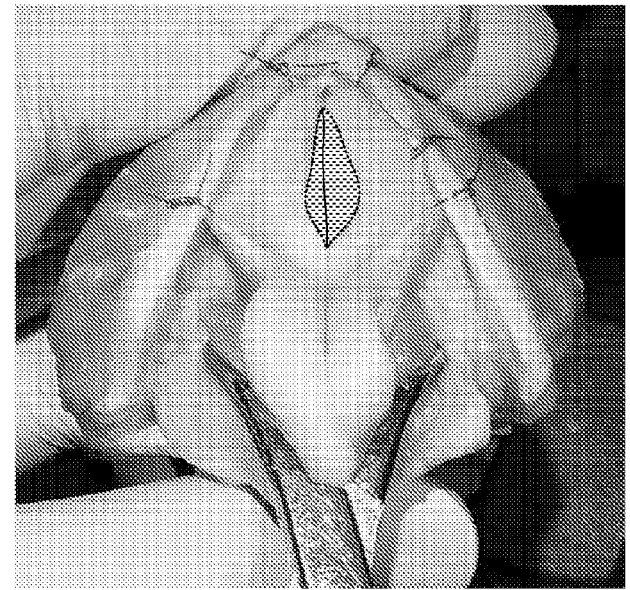

Referring to FIG. 4C, the vocal folds were adducted using a sharp clamp to bring the arytenoids into a position that allowed the right vocal fold to be driven into vibration (phonated) when air flows were initiated. The vocal cords were adducted 3 times—before the vocal folds were stiffened (to confirm that the larynx is suitable for use), after the vocal fold stiffenings, and lastly after the injection of a gel. First, air flow was ramped up and down rapidly (starting at zero flow each time) 5 times (1-2 second) to measure the minimum driving pressures required to produce phonation (phonation threshold pressure; PTP). The right vocal fold was also vibrated with a gradual pressure increase from PTP up to a point at which phonation was judged to become aperiodic (overdriven) to measure the relationship between driving pressure and fundamental frequency (F0) of vibration.

Imaging of calf vocal-fold vibration during induced phonation was accomplished by attaching a Phantom® v7.3 high-speed video camera (Vision Research, Inc., Wayne, N.J.) to the optical adaptor of the operating microscope. This enabled magnified high-quality color imaging at 12-bit quantization with a CMOS image sensor. HSV data were recorded at 4000 images per second with maximum integration time and a spatial resolution of 448 horizontal×424 vertical pixels to capture an approximately 2 $cm^2$ target area. Illumination was provided by the Leica® F40 surgical microscope with integrated 300 W Xenon arc light source. Each high-speed video data segment consisted of 1000 images (250 ms).

Air pressure and high-speed imaging data were reviewed immediately after the initial testing to ensure that PTPs were within expected limits and that the right vocal fold was displaying normal deformation of the mucosal surface (mucosal wave) during vibration.

After successful initial testing of the right vocal fold, referring to FIG. 4B, the vocal fold was then injected with approximately 0.04-0.1 ml of a specific gel into the superficial lamina propria (SLP) using a 25 gauge Zeitels Vocal-fold Infusion needle (Endocraft®, LLC, Providence, R.I.). All of the gels were dyed blue to make them easily visible on imaging (shown as dotted area in FIG. 4B), and the amounts injected were scaled proportionally to the size of the musculo-membranous portion of vocal folds in each larynx tested. Testing of the right vocal fold vibration was then repeated as described above.

Data analysis was done in two stages. First, recordings of high-speed imaging were reviewed to determine if the injected area of right vocal fold was displaying deformation of the mucosal surface (mucosal wave). Materials that did not transmit a mucosal wave were not evaluated further, because this indicated deficient function. The second stage of data analysis was conducted for materials that did transmit a mucosal wave including assessments of PTP and range of F0.

Example 2

Testing of Various Vocal Peg Hydrogel Compositions in the Calf Larynx Ex-Vivo Model Vocal PEG hydrogels can be readily produced with various elastic and viscous shear modulus (G' and G") values that fall within the range that transmit mucosal waves, and have different longevity or residence times once implanted in the vocal folds. These different formulations can be matched to the vocal needs of different types of patients with voice disorders.

PEG hydrogels were prepared using semi-InterPenetrating Network (semi-IPN) technology by photopolymerization of polyethylene glycol diacrylate (PEG-DA; SunBio Inc., Orinda, Calif.) in the presence of polyethylene glycol (PEG; Aldrich, St. Louis, Mo.). Molecular weight of both the polymers was 10 kDa.

Briefly, aqueous solutions of PEG and PEG-DA (both 100 mg/mL) were made in sterile PBS by adding 100 mg of polymer to 1 mL of PBS. The solutions were then mixed in a predetermined volumetric ratio of PEG-DA:PEG (e.g., 3:7 to prepare PEG30). PEG hydrogels with different stiffness values were made by varying the ratio of PEG-DA:PEG used to make the gels. The precursor solution (1 mL) was gelled for 200 seconds using 0.05% (w/v) of Irgacure® 2959 (Ciba, Tarrytown, N.Y.) as the photoinitiator. An Omnicure S2000® lamp (EXFO Lifesciences, Mississauga, Canada) that generated ultra-violet light of intensity 2 mW/cm$^2$ (measured at 365 nm) was used for the gelation. The process may be modified to prepare large amounts (>1 mL) of gels with similar physicochemical properties.

Post-gelation, the gels were incubated in excess PBS (volume=9× volume of the gel) for 24 hours at 37° C. The swollen gels were progressively sheared through needles of decreasing bore size to make them injectable through a 25-gauge needle. The gels were stored at 4° C. sealed in a capped syringe until further use.

Six different PEG hydrogel compositions with varying mechanical properties (as measured by the elastic shear modulus, G', and viscous shear modulus, G", at 37° C. and 10 Hz) were synthesized using the above method and tested. Specifically, the following PEG hydrogels were tested: PEG30 (G'=26 Pa, G"=5 Pa), PEG34 (G'=42 Pa, G"=8 Pa), PEG37 (G'=88 Pa, G"=21 Pa), PEG40 (G'=112 Pa, G"=19 Pa), PEG43 (G'=143 Pa, G"=30 Pa), and PEG50 (G'=183 Pa, G"=30 Pa).

The photopolymerization process employed here is a radical polymerization process that contributes to the batch-to-batch variability in the mechanical properties of the PEG gels made using this process. Table 2 lists a typical range of G' and G" values that were obtained for the PEG hydrogels made using the above process.

TABLE 2

Typical range of G' and G" values for selected PEG hydrogels

| PEG Hydrogel | PEG-DA:PEG Ratio (v/v) | G' Range | G" Range | Estimated In vivo Residence Time |
|---|---|---|---|---|
| PEG30 | 30:70 | 15 Pa to 35 Pa | 5 Pa to 11 Pa | ≤2 months |
| PEG37 | 37:63 | 75 Pa to 88 Pa | 16 Pa to 21 Pa | 2-4 months |
| PEG43 | 43:57 | 125 Pa to 149 Pa | 27 Pa to 32 Pa | 4-6 months, or more |

Hydrogels having similar G' values as PEG30, were also prepared using similar procedure as outlined above. These polymers are listed in Table 3.

TABLE 3

Hydrogels with G' Values Similar to PEG30 - Prepared with Other Polymers

| Name | Cross-linkable component (X) | Non-crosslinkable component (Y) | Volumetric fraction of X before gelation (f) | Elastic Shear Modulus G' (Pa) |
|---|---|---|---|---|
| PEG-HA | PEG-diacrylate (10 kDa) from SunBio Conc.: 100 mg/mL | Hyaluronic Acid (HA; 74 kDa) from LifeCore Biomedical Conc.: 1 mg/mL | 0.3 | 22 Pa |
| PEG-Dextran | PEG-diacrylate (10 kDa) from SunBio Conc.: 100 mg/mL | Dextran (100 to 200 kDa) from Sigma Conc.: 20 mg/mL | 0.3 | 24 Pa |
| PEG-Alginate | PEG-diacrylate (10 kDa) from SunBio Conc.: 100 mg/mL | Sodium alginate (viscosity: 20,000 to 40,000 cps) from Aldrich Conc.: 0.5 mg/mL | 0.28 | 25 Pa |
| PEG-Polylysine | PEG-diacrylate (10 kDa) from SunBio Conc.: 100 mg/mL | Poly-L-Lysine (70 to 150 kDa) from Fluka Biochemika | 0.28 | 21 Pa |

The viscoelastic shear properties of all of the PEG hydrogel compositions were measured at 37° C. and at low frequencies (1 Hz to 10 Hz) using an AR-2000 rheometer (TA Instruments, Inc., New Castle, Del.). A cone-and-plate geometry was used to apply oscillatory shear to the gel samples using an acrylic cone (60 mm diameter, 2° angle) and a flat metallic peltier plate heated to 37° C. The hydrogels were placed between the heated plate and the cone so that a manufacturer-specified gap of 61 µm was maintained between the cone and the plate. The hydrogels were subjected to an oscillatory shear at 1 Hz for 2 minutes to equilibrate the entire hydrogel to a uniform temperature of 37° C. Strain sweep tests were done to ensure that the shear property measurements were done in the linear region of the stress-strain curve.

The viscoelastic shear properties are independent of the percentage strain in the linear region. A target shear strain value was therefore identified by measuring the viscoelastic shear properties as a function of percentage strain applied (0.6% strain was typically used to measure the shear properties using a frequency sweep). Measurements of the shear properties were then made by systematically varying the frequency from 1 to 10 Hz. The elastic shear modulus (G') and viscous shear modulus (G") at 10 Hz and 37° C. were used as a measure of the mechanical properties of the gels used in this study.

PEG hydrogels were formulated to produce a range of elastic shear modulus (G'; measured at 10 Hz) values starting with the lowest G'=26 Pa (PEG30). Results from high-speed imaging of phonation in the calf larynx demonstrated that PEG hydrogel compositions transmitted mucosal waves up to a G'=143 Pa (PEG43).

Results for PTP and range of F0 further differentiated the function of the PEG hydrogels that transmitted mucosal wave activity. PEG30 (G'=26 Pa) required a PTP that was approximately 2.8 cm H$_2$O (21%) higher than baseline (pre-injection) and demonstrated an F0 range of 85 Hz (increase of 77% above the lowest F0) across variation in driving pressures. PEG43 (G'=143 Pa) required an increase in PTP of approximately 4.8 cm H$_2$O (92%) over baseline and displayed an F0 range of 36 Hz (increase of 38% above the lowest F0) across variation in driving pressures.

PEG gels with higher stiffness (G') values were formulated by increasing the crosslinked component (PEG-DA) of the gels. Higher crosslinking in polymeric hydrogels can yield materials with higher G' values and longer in vivo residence times. As an example, increasing the crosslinking in a hydrogel can prolong the in vivo residence time of soft-tissue filler materials (Adams, M. E. et al., "A Risk-Benefit Assessment of Injections of Hyaluronan and its Derivatives in the Treatment of Osteoarthritis of the Knee," Drug Safety, 2000; 23:115-130; Christensen, L., "Normal and Pathologic Tissue Reactions to Soft-tissue Gel Fillers," Dermatologic Surgery, 2007; 33:S168-S175). Furthermore, non-degradable gels (i.e., gels with extremely long in vivo residence time) have been prepared earlier (West, J. L. et al., "Separation of the arterial wall from blood contact using hydrogel barriers reduces intimal thickening after balloon injury in the rat: the roles of medial and luminal factors in arterial healing," Proc. Natl. Acad. Sci., USA, 1996; 93:13188-93) using the same PEG-DA as used in the gels reported here. Such gels may be considered an extreme case of the semi-IPN PEG gels reported here with 100% PEG-DA and 0% PEG.

Based on the above, the in vivo residence time of PEG gels with higher G' values is expected to be longer than that of the PEG gels with lower G' values. Specifically, the in vivo residence times of PEG30 is expected to be ≤2 months, that of PEG37 is expected to be ≤4 months, and that of PEG43 is expected to be ≤6 months. In each case, these are the minimum times, and the implant can last longer.

Example 3

Testing of PEG30 and Biomechanically Similar Materials in a Cow Larynx Model

An ex vivo bovine larynx model was used to the evaluate effects of gel stiffness on mucosal wave amplitude, as a measure of vocal fold pliability. Adult cow cadaver larynges were prepared by cutting a 1 cm by 3 cm window in the thyroid lamina and then removing a block of the thyroarytenoid muscle to expose the deep surface of the vocal ligament, a layer of collagenous tissue between the SLP and the thyroarytenoid muscle. The ligament was opened with microscissors and the soft contents of the lamina propria were carefully removed over the entire extent of the vocal fold, leaving only the thin and transparent epithelium with minimal attached SLP. The test materials were layered behind the epithelium in volumes equal to the volume of the removed lamina propria (~0.25 ml), resulting in a layer of gel 2-3 mm thick. An oval piece of stiff latex sheet was placed behind the test material in the location previously occupied by the vocal ligament. The remaining cavity through the muscle and thyroid cartilage was then filled with stiff alginate for measurement of mucosal wave amplitude using high speed imaging. The alginate, dam, and test material were easily removed for sequential testing of different hydrogels in the same biomechanical environment.

Different hydrogels biomechanically similar to PEG30 (as judged by measuring their elastic shear modulus, G') were prepared by systematically varying the concentration, volumetric ratio in the precursor solution, and the polymer used for the crosslinkable and non-crosslinkable component. We were able to identify four materials that can be considered mechanically equivalent to PEG30 based on elastic shear modulus (see Table 3). These materials were also tested in the cow larynx model using the procedure outlined above. All the materials were tested in a single cow larynx with each material being tested twice. Multiple high speed video clips from tests controlled for sub-glottal pressure were selected and maximum mid-membranous vocal fold excursion was measured using a MATLAB program.

Figure 5:
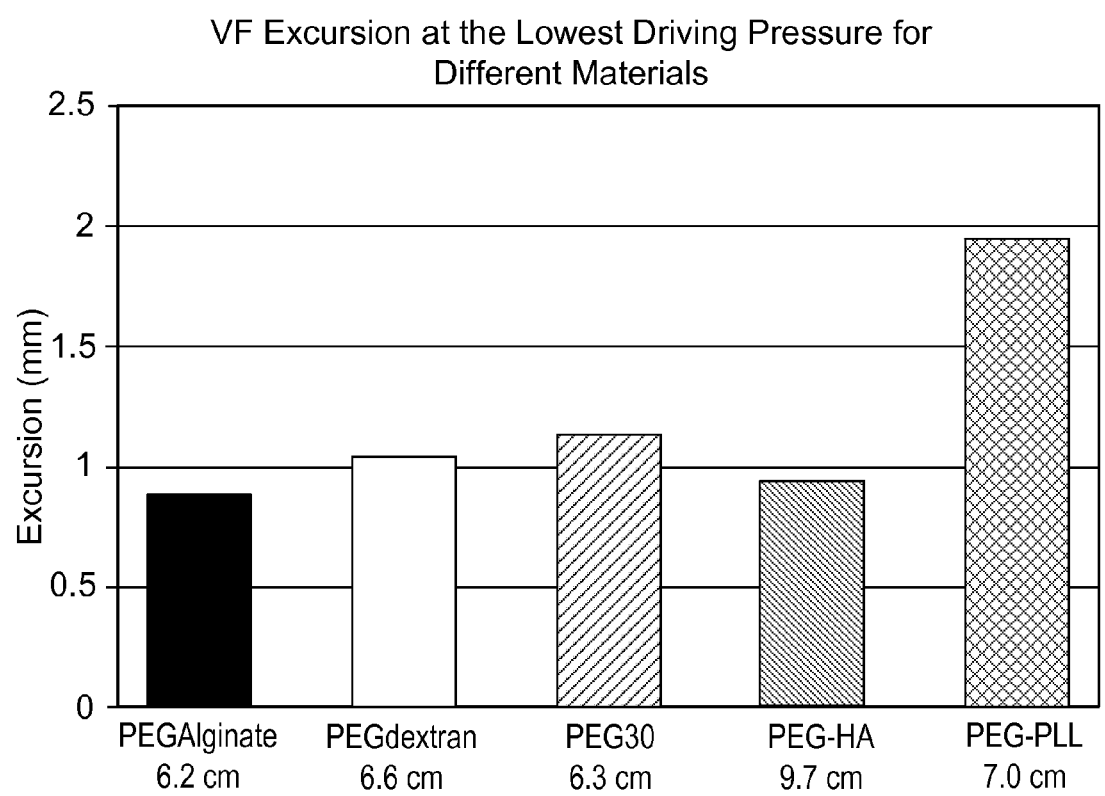
FIG. 5 is a chart showing vocal fold excursion in a cow larynx model upon implantation of different materials.

FIG. 5 shows the maximum vocal fold (VF) excursion for the different materials at the lowest driving pressure that was able to produce vibration in the VFs. Referring to FIG. 5, PEG-PLL (7.0 cm) had an excursion of about 1.9 mm, PEG-HA (9.7 cm) had an excursion of about 0.9 mm, PEG 30 (6.3 cm) and PEG dextran (6.6 cm) had excursions of about 1.2 mm and 1.1 mm, respectively, and PEG alginate (6.2 cm) had an excursion of about 0.8 mm.

Example 4

Large Scale Preparation of "PEG30" PEG-Hydrogel Composition

PEG30 hydrogels were also manufactured on a larger scale (~120 mL final product/batch) by modifying the process parameters.
Outline of Synthesis Methods
1. The component solutions were prepared as follows:
   a. Aqueous solution of PEG (100 mg/mL) were made by adding 78.9±0.1 mL sterile PBS to 7.888±0.003 g PEG followed by stirring at 250 rpm for 10 min.

b. Aqueous solution of PEG-DA (100 mg/mL) were made in sterile PBS by adding 31.4±0.1 mL PBS to a 3.143±0.003 g PEG-DA followed by stirring at 250 rpm for 5 min. The solution of PEG-DA was made fresh and kept protected from light till further use.

c. Solution of the PI (50 mg/mL) was made in 70% (v/v) ethanol by adding 2.076±0.001 mL 70% ethanol to 0.1038±0.0003 g of PI followed by mixing by shaking the vial by hand for 40 to 50 seconds.

d. All solutions were filtered through a 0.2 μm filter before use in a sterile hood.

2. PEG-DA and PEG solutions were mixed in a 3:7 ratio (v:v) by adding 29.7±0.01 mL PEG-DA solution to 69.3±0.01 mL PEG solution with continuous stirring.

3. PI solution (0.99±0.001 mL) was added to the PEG-DA: PEG solution with continuous stirring to prepare the precursor solution.

4. 90±0.1 mL of the precursor solution was added to a 250 mL plastic beaker in preparation for the gelation process.

5. UV light (320 to 500 nm) was shone for 200 s while the solution was being stirred using a magnetic stir bar. An EXFO S2000 lamp that emits UV light of intensity 3±0.1 mW/cm$^2$ (measured at 365 nm) was used for this process. After gelation for 200 s, the stirring was stopped, the stir bar was removed and the partially gelled liquid was exposed to UV light for another 300 s. At this point gelation was complete and a solid block of gel was obtained.

Incubation, Swelling, and Shearing

1. The gel block (90 mL) was then incubated in PBS (810±1 mL) in a biological incubator at 37±0.1° C. and in an atmosphere of 5%±0.2% $CO_2$ for 24±0.1 h.

2. After the incubation is complete, the swollen gel block (approximately 120 mL) was removed from the incubator.

3. The swollen gel was cut into 3 pieces using a sterile knife, and each piece was put in a Luer-lok syringe (60 mL). Injecting the gel block through a needle provided shearing of the gel and therefore, each piece of the gel was injected into another Luer-lok syringe (60 mL). To achieve the required amount of shearing, the process was repeated using needles of progressively decreasing bore sizes. Specifically, 16, 18, 20, and 22 gauge needles were used for shearing the gels with gels being sheared through each needle twice, to achieve the required amount of shearing.

4. The gel thus obtained at the end of the shearing process was added into the bore of an unused, sterile Luer-lok syringe (60 mL) and capped with a syringe cap. As needed, the gels were dispensed into syringes of smaller volume and capped with a syringe cap. The gel-containing syringes were stored at 4° C. until further use.

Example 5

Biodegradation Studies

We have evaluated the biocompatibility and biodegradation of PEG30 implants in the vocal-folds of ferrets (see Table 4). These studies demonstrated that the PEG30 material does not migrate outside the injection area by histological evaluation and does not generate unusual or unexpected foreign-body reaction or adverse systemic effects. The PEG30 is biodegraded by macrophage-mediated breakdown.

TABLE 4

Ferret Studies Using PEG30

| Animal Model | Total # of Animals | Site of Implantation | Objective of the Study | Survival Time Periods |
|---|---|---|---|---|
| Ferret | 20 | Vocal-fold | Evaluation of in vivo toxicity and residence time of PEG30 | 1, 2, 4, & 12 weeks |

PEG30 was prepared using methods similar to those described earlier in Example 2. All gels were prepared and handled in sterile conditions before injection.

In Vivo Safety Studies

Ferret Vocal-fold Implantation Study

Objective:

The purpose of this study was to assess the biocompatibility of PEG30 over a 12 week period when injected into ferret vocal-folds. Ferret was chosen as the small animal model for this study because the jaw-neck anatomy and the larger size of its vocal-folds as compared to that of mice or rats allowing for easier microlaryngoscopic surgical access to the vocal-fold and hence facilitate a more controlled and localized injection.

Methods:

PEG30 was injected (average ~9 μL) unilaterally into the VF of 20 healthy adult male ferrets (Marshall Farms, North Rose, N.Y.) using a miniaturized version of the needle that is used routinely in the clinic for making injections in human VFs. The contralateral untreated vocal-fold was used as an internal control. The ferrets were observed for 1 week (n=5), 2 weeks (n=1), 4 weeks (n=13), and 12 weeks (n=1), and then euthanized. Except for 5 ferrets euthanized 4 weeks post-injection, the larynx was harvested for evaluation in the remaining 15 ferrets post-euthanasia. In life, VFs were periodically examined with an operating microscope for any signs of inflammation, and vibratory function was evaluated by inducing phonation using humidified air introduced from below the VFs using a tracheal needle. Harvested larynges were processed and examined by high resolution MRI to identify the location of the PEG30 and by light microscopy by a certified ear, nose, and throat pathologist to evaluate tissue responses. Injected and non-injected VFs were compared. For microscopic evaluation, 5-micron thick coronal sections were cut from paraffin-embedded VFs, stained with hematoxylin & eosin, and examined using a 40× objective. Up to four sections were examined from each ferret.

Results:

All animals survived to their scheduled euthanization date.

In life, there were no signs of inflammation in any animal, and the injected VF vibrated with little or no difference in pliability compared to the contralateral untreated VF.

Figure 6:
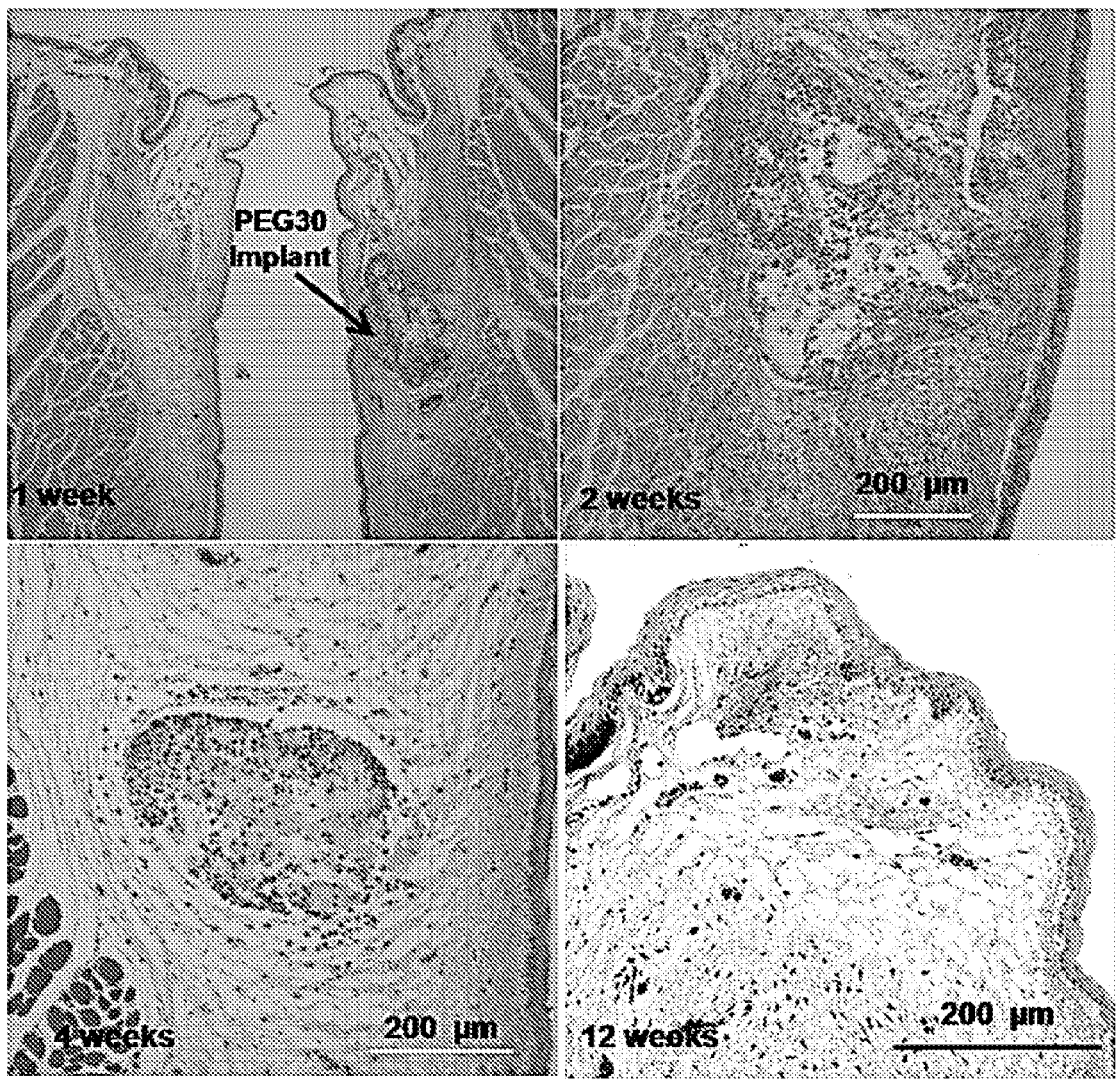
FIG. 6 is a series of microscopy images of a histological evaluation of PEG30 injected into ferret vocal-folds.

At one week post-injection, ex vivo MRI identified PEG30 in the injected vocal-fold of all 5 animals. Referring to FIG. 6, there was significant macrophage infiltration at the implantation site including and surrounding the PEG30, occasionally accompanied by lymphocytes and plasma cells (1/5 animals), mild fibrosis (2/5 animals), and/or 1 or 2 giant cells (2/5 animals). Neutrophils were not present in any animal. These findings are typical of a foreign-body reaction. The entire reaction was localized to the site of PEG30 injection.

At 2 and 4 weeks post-injection, histopathologic findings were similar but with less residual PEG30, fewer macrophages, and less fibrosis. No neutrophils or giant cells were observed. At 4 weeks, no macrophages were observed in one animal, and mild fibrosis and occasional giant cells were observed in 2/6 animals.

At 12 weeks, PEG30 was completely resorbed and there was no evidence of a foreign body reaction (only one animal assessed at this time).

No capsule formation around the implant or significant changes in vascularity in or around the implant was noted in any animal at any time post-injection.

Conclusions:

PEG30 was considered to be biocompatible, based on the fact that it produced a short term foreign-body response characterized by macrophage infiltration, occasionally accompanied by lymphocytes, plasma cells, and/or mild fibrosis, without evidence of acute inflammation (e.g., neutrophils) or chronic inflammation (e.g., neovascularization or capsule formation) in any animal. The foreign-body response decreased with time in parallel with the amount of residual PEG30.

PEG30 was considered to be biodegradable, based on the fact that it was partially resorbed by 4 weeks post-injection and completely absent by 12 weeks post-injection.

Referring to FIG. 6, image A showed residual PEG30 (arrow) 1 week after injection; image B showed residual PEG30 and accompanying cellular reaction at 2 weeks post-injection; image C showed a Masson's Trichrome image showing residual PEG30 at 4 weeks post-injection (note the decrease in cellular reaction and lack of fibrosis); and image D showed ferret VFs 12 weeks post-injection of PEG30 (note absence of residual PEG30, cellular reaction and minimal fibrosis or other damage to the vocal-folds).

Example 6

Rabbit Study to Estimate In Vivo Residence Time

Objective:

The purpose of this study was to compare the in vivo residence time of two preparations, PEG30 (G'=28 Pa and G"=8 Pa) and PEG43 (G'=149 Pa and G"=32 Pa).

Methods:

PEG30 and PEG43 were injected intra-cutaneously (one injection of 400 μL each) on the dorsal surface of an adult female New Zealand White Rabbit (Charles River Labs, Wilmington, Mass.) using a 25 gauge needle. The rabbit was euthanized after one week, the implants were recovered and the tissue response to the implant was evaluated using histological analysis.

Figure 7A:
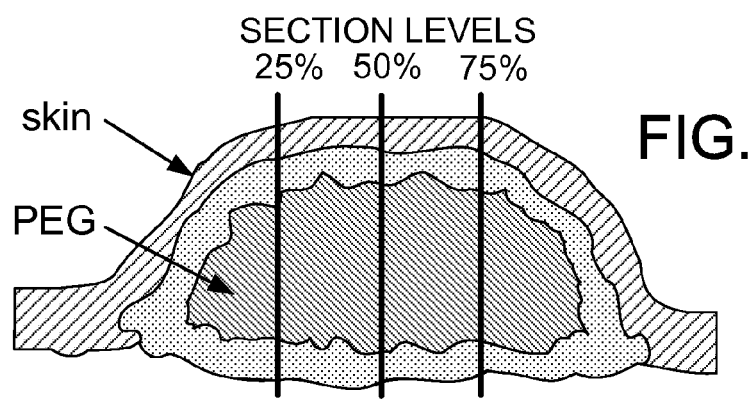
FIGS. 7A-7C show histological images obtained from recovered implants of different hydrogel compositions in a rabbit model and the analysis of the images.
Figure 7B:
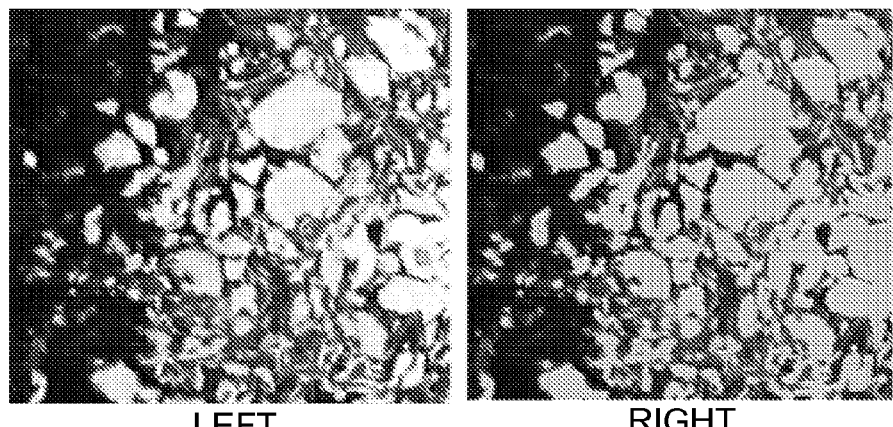

Referring to FIG. 7A, Recovered tissue specimens (e.g., histological sections) were blocked at 3 levels as shown in FIG. 7A. To measure the amount of residual material, 5-micron thick sections were cut from paraffin-embedded blocks, stained with hematoxylin & eosin, and were imaged using a Canon G9 digital camera in macro mode (14 MB images). FIG. 7B shows identification of PEG based on color and intensity of the residual material in the hematoxylin and eosin stained tissue sections. The left image in FIG. 7B shows a typical section appearance including many irregular, acellular areas with lightly stained amorphous material, which are characteristic of residual gel. The right image in FIG. 7B shows the amorphous areas that have been selected for measurement (light gray).

Referring again to FIG. 7B, the PEG was segmented from adjacent tissue based on color and intensity using Adobe Photoshop (command sequence: Open file>Select (position cursor on amorphous material)>Color Range (adjust parameters to select amorphous material)>Bucket tool fill of selected areas (contiguous parameter set to off) >Copy>New>Paste>Save). The injected substances were identifiable as irregular shaped, cell-free pockets containing lightly stained amorphous material. These regions were clearly distinguishable from adjacent, intensely stained subcutaneous tissue. Identified PEG as selected using the color range function is depicted in light gray in the right panel of FIG. 7B. The total area of the identified PEG was then measured using ImageJ software (command sequence: Open file>Image>Adjust threshold (adjust to select areas identified in Photoshop)>Analyze>Set Scale (calibration step)>Analyze Particles (find total area of all regions)). The areas occupied by PEG in the 3 sections were summed for each specimen to compare the relative amounts of residual PEG30 and PEG43.

Figure 7C:
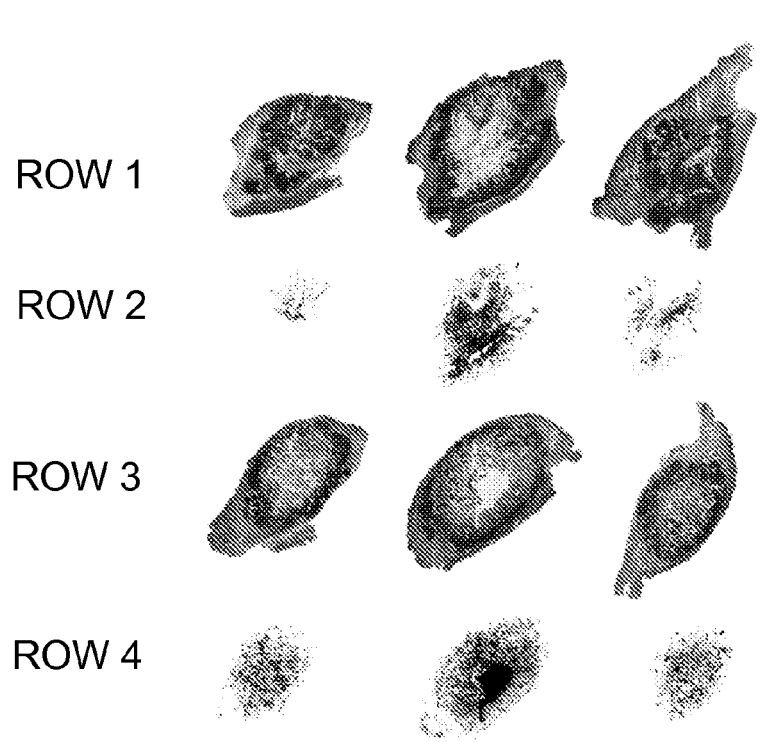

Results:

For equal amounts (400 μL) of intra-cutaneous injected material, more PEG43 (46.4 mm$^2$) was seen in tissue sections at 1 week following injection as compared to PEG30 (26.8 mm$^2$) (FIG. 7C and Table 5). Referring to FIG. 7C, the top row shows PEG 30 sections at 25%, 50% and 75% levels, H&E stain; Row 2 shows the residual material identified in the sections in row 1, shown separately. The total area of the identified material was then measured and summed; Row 3 shows PEG 43 sections at 25%, 50% and 75% levels, H&E stain; Row 4 shows residual material in row 3 as identified by image processing. The amount of residual PEG43 at one week post-injection, as estimated by the above described method, was about 1.7 times that of PEG30. Assuming a constant rate of degradation for the two gels, it may be extrapolated that PEG43 has a longer in vivo residence time than PEG30.

Conclusions:

The stiffer gel (PEG43) had more residual amount at the one week time-point in rabbit intra-cutaneous tissue as compared to the softer gel (PEG30); PEG43 thus seems to have a longer in vivo residence time than PEG30.

TABLE 5

Areas Occupied by PEG30 and PEG43 in Three Sections
Cross-sectional area of residual material (mm$^2$)
Level of section through injection site

|  | 25% level | 50% level | 75% level | Total |
| --- | --- | --- | --- | --- |
| PEG 30 | 1.28 | 21.29 | 4.27 | 26.84 |
| PEG 43 | 9.66 | 28.16 | 8.58 | 46.40 |

Example 7

Self-Assessment Questionnaire

A subject can be assessed using the following self-assessment questionnaire and interview questions:

Occupation(s): _____

Specify: full-time, part-time, unemployed, retired, or disabled

Vocal Concerns/Symptoms:

1) Describe your present vocal difficulty.

When did you first notice your vocal problem?

Did it begin suddenly, gradually, or are you unsure? (Circle the appropriate response)

2) Were there any events or circumstances that occurred with the onset of your vocal difficulty (e.g., upper respiratory infection, surgery, emotional stress/anxiety, chemical exposure, accident, increased voice use, vocal abuse (yelling/screaming), change in job)?

3) How does your voice sound today, compared to recently?
Same Better Worse
If better or worse, is there any factor you contribute to the change in voice today?
4) Please indicate what vocal symptoms apply to you.
_____ NONE
_____ Hoarseness (raspy or scratchy sound)
_____ Breathiness in speaking voice
_____ Fatigue (voice tires or quality changes)
_____ Voice breaks
_____ Whisper only (total loss of voice)
_____ Trouble speaking softly
_____ Trouble speaking loudly
_____ Trouble singing
_____ Sore throat
_____ Tickling or choking sensation
_____ Lump in throat
_____ Difficulty swallowing
_____ Voice is lower
_____ Voice is higher
_____ Voice is weaker
_____ Vocal strain
_____ Frequent throat clearing
_____ Frequent dry throat
_____ Frequent coughing
_____ Nasality
_____ Difficulty with the telephone
_____ Periods of normal voice Do these symptoms worsen at certain times of the day (e.g., morning, afternoon or evening)?

Do these symptoms worsen during particular seasons (e.g., winter, spring, summer, fall)?

Voice Use:
5) On average, how many hours/day do you use your voice?
6) Review the list below and check the activities that apply to you.
_____ singing
_____ acting
_____ parent to young children
_____ lecturing/teaching/speaking for an audience
_____ cheerleader
_____ clergy activities
_____ caretaker for someone with a hearing impairment
_____ phone operator
_____ auctioneer
_____ choral director
_____ sports enthusiast
_____ politician
_____ yelling/screaming
_____ whispering
_____ voice use with strenuous exercise (e g, running)
_____ speaking over background noise
_____ throat clearing
_____ excessive coughing
_____ imitating other people's voices
_____ making "noises" with your voice
_____ other (explain)

In addition, the subject's past medical history, including past surgery to the larynx, past medical procedures, CT/MRI imaging of the head and/or neck, past and present medical conditions, current medications, past or present voice therapy, as well as alcohol, cigarette, drug, caffeine, and water consumption can be ascertained.

Example 8

Voice Related Quality of Life Measure

To learn more about how a voice problem can interfere with a subject's day-to-day activities, the subject's voice-related quality of life measure can be determined using the following questionnaire and scale:

Please answer all questions based on what your voice has been like over the past two weeks. There are no "right" or "wrong" answers.

Considering both how severe the problem is when you get it, and how frequently it happens, please rate each item below on how "bad" it is (that is, the amount of each problem that you have). Using the following scale for rating the amount of the problem.

1=None, not a problem
2=A small amount
3=A moderate (medium) amount
4=A lot
5=Problem is as "bad as it can be"

Because of my voice . . .

| | None | A small amount | A moderate amount | A lot | "Bad as it can be" |
|---|---|---|---|---|---|
| 1. I have trouble speaking loudly or being heard in noisy situations. | 1 | 2 | 3 | 4 | 5 |
| 2. I run out of air and need to take frequent breaths when talking. | 1 | 2 | 3 | 4 | 5 |
| 3. I sometimes do not know what will come out when I begin speaking. | 1 | 2 | 3 | 4 | 5 |
| 4. I am sometimes anxious or frustrated (because of my voice). | 1 | 2 | 3 | 4 | 5 |
| 5. I sometimes get depressed (because of my voice). | 1 | 2 | 3 | 4 | 5 |
| 6. I have trouble using the telephone (because of my voice). | 1 | 2 | 3 | 4 | 5 |
| 7. I have trouble doing my job or practicing my professions (because of my voice). | 1 | 2 | 3 | 4 | 5 |
| 8. I avoid going out socially (because of my voice). | 1 | 2 | 3 | 4 | 5 |
| 9. I have to repeat myself to be understood. | 1 | 2 | 3 | 4 | 5 |
| 10. I have become less outgoing (because of my voice). | 1 | 2 | 3 | 4 | 5 |

(See, Hogikyan N D and Rosen C A. A review of outcome measurements for voice disorders. Otolaryngology-Head and Neck Surgery 2002; 126(5) 562-72.)

Other Embodiments

A number of embodiments of the invention have been described. Nevertheless, it will be understood that various modifications may be made without departing from the spirit and scope of the disclosure. Accordingly, other embodiments are within the scope of the following claims.

What is claimed is:

1. A method of providing a customized vocal treatment to a subject having a vocal dysfunction caused by a diminished pliability or absence of phonatory mucosa, the method comprising
assessing both a cause of the subject's vocal dysfunction and the subject's vocal needs;
selecting a specific vocal implant to provide a mucosal tissue with sufficient pliability to produce an approximate desired level of dynamic variation of vocal parameters of pitch or phonation threshold pressure, or both and vocal control in the subject based on both the cause of the subject's vocal dysfunction and the subject's vocal needs, wherein the vocal implant is a liquid, a gel, or a solution of one or more polymers; and implanting the selected vocal implant in a location within glottal, supraglottal, subglottal, or pharyngeal mucosal tissue in the subject that achieves the desired level of dynamic variation of vocal parameters and vocal control to provide a customized vocal treatment specific to the subject's vocal dysfunction and needs.

2. The method of claim 1, wherein the assessing comprises determining any one or more of a deficit in a primary mode of sound production, a deficit in structural anatomy, or a deficit in vocal function.

3. The method of claim 2, wherein the assessing comprises using any one or more of: high-speed endoscopic laryngeal imaging, laryngeal stroboscopy, acoustic and aerodynamic measures of vocal function, standard interview, and self-reporting of the impact of the vocal deficit on daily function using a standardized self-assessment scale.

4. The method of claim 2, wherein the deficits in structural anatomy or vocal function are due to one or more of an anatomical structure that is missing, and an anatomical structure that is functionally impaired.

5. The method of claim 2, wherein the deficits in structural anatomy or vocal function are due to at least one of a loss of muscle, loss of ligament, and loss of the superficial lamina propria of normal phonatory mucosa.

6. The method of claim 1, wherein the vocal implant is placed into mucosal tissue under epithelium of a region of the subject's supraglottis, subglottis, or pharynx in a location and in an amount that provides aerodynamically-driven mucosal vibration, wherein the supraglottal, subglottal, or pharyngeal mucosa is converted into a phonatory sound source.

7. The method of claim 1, wherein the vocal implant is placed into mucosal tissue under epithelium of one or both vocal folds of the glottis.

8. The method of claim 1, wherein the vocal implant has an elastic shear modulus (G') within a range of 0 to 150 pascals.

9. The method of claim 1, wherein the vocal implant has an in vivo residence time that is inversely related to the elastic shear modulus (G') of the vocal implant.

10. The method of claim 1, wherein the vocal implant is tuned based on the assessing.

11. The method of claim 1, wherein the vocal implant comprises a network of one or more polymers.

12. The method of claim 1, wherein the vocal implant comprises at least one crosslinked polymer.

13. The method of claim 1, wherein the vocal implant comprises a crosslinked polymer and a non-crosslinked polymer.

14. The method of claim 1, wherein the vocal implant comprises a crosslinked poly(ethylene glycol) derivative and a non-crosslinked polymer.

15. The method of claim 13, wherein the non-crosslinked polymer comprises poly(ethylene glycol), hyaluronic acid, alginate, poly(lysine), dextran, or combinations thereof.

16. The method of claim 12, wherein prior to crosslinking, the crosslinked poly(ethylene glycol) derivative is poly(ethylene glycol)diacrylate.

17. The method of claim 1, wherein the vocal implant comprises polysaccharides, water-soluble synthetic polymers, proteins and their derivatives, or combinations thereof.

18. The method of claim 1, wherein the vocal implant further comprises a biologically active agent.

19. The method of claim 1, wherein the vocal implant comprises a crosslinked poly(ethylene glycol) derivative and a non-crosslinkable polymer selected from the group consisting of polysaccharides, water-soluble synthetic polymers, and proteins and their derivatives.

20. The method of claim 13, wherein the crosslinked polymer comprises an acrylate derivative and the non-crosslinked polymer comprises a water-soluble polymer.

21. The method of claim 13, wherein the crosslinked polymer comprises at least one of hyaluronic acid methacrylate, crosslinkable derivatives of dextrans, crosslinkable derivatives of hyaluronic acid, crosslinkable derivatives of alginates, crosslinkable derivatives of gelatins, crosslinkable derivatives of elastins, crosslinkable derivatives of collagens, crosslinkable derivatives of celluloses, crosslinkable derivatives of methylcelluloses, crosslinkable derivative of polyalkylene glycol, crosslinkable derivative of polyethylene glycol, and polyethylene glycol diacrylate; and the non-crosslinked polymer is selected from the group consisting of any one or more of polyethylene glycol (PEG), poly(lysine), hyaluronic acid (HA), dextrans, alginates, gelatins, elastins, collagens, celluloses, methylcelluloses, and derivatives thereof.

22. The method of claim 13, wherein the crosslinked polymer comprises an acrylated derivative of dextrans, acrylated derivatives of hyaluronic acid, acrylated derivatives of alginates, acrylated derivatives of gelatins, acrylated derivatives of elastins, acrylated derivatives of collagens, acrylated derivatives of celluloses, acrylated derivatives of methylcelluloses, acrylated derivative of polyalkylene glycol, acrylated derivatives of polyethylene glycol, and polyethylene glycol diacrylate; and the non-crosslinked polymer is selected from the group consisting of any one or more of polyethylene glycol (PEG), poly(lysine), hyaluronic acid (HA), dextrans, alginates, gelatins, elastins, collagens, celluloses, methylcelluloses, and derivatives thereof.

23. The method of claim 1, wherein the vocal parameter is pitch.

24. The method of claim 8, wherein the vocal implant comprises a hydrogel having a G' of 0 to 50 Pa and a residence time in vivo of from about 1 day to about 2 months, a hydrogel having G' of 50 to 100 Pa and a residence time in vivo of about 2 to about 4 months, or a hydrogel having a G' of 100 to 150 and a residence time in vivo of over 4 months.

25. The method of claim 8, wherein the vocal implant comprises a hydrogel having a G' of 15 to 35 Pa and a residence time in vivo of from about 1 day to about 2 months, a hydrogel having G' of 75 to 88 Pa and a residence time in vivo of about 2 to about 4 months, or a hydrogel having a G' of 125 to 149 Pa and a residence time in vivo of over 4 months.

* * * * *